United States Patent
Jonckers et al.

(10) Patent No.: US 8,431,588 B2
(45) Date of Patent: Apr. 30, 2013

(54) CYCLOPROPYL POLYMERASE INHIBITORS

(75) Inventors: Tim Hugo Maria Jonckers, Mechelen (BE); Pierre Jean-Marie Bernard Raboisson, Mechelen (BE); Koen Vandyck, Mechelen (BE)

(73) Assignees: Janssen Products, LP, Horsham, PA (US); Medivir AB, Huddinge (SE)

( * ) Notice: Subject to any disclaimer, the term of this patent is extended or adjusted under 35 U.S.C. 154(b) by 119 days.

(21) Appl. No.: 12/999,263

(22) PCT Filed: Jul. 1, 2009

(86) PCT No.: PCT/EP2009/004748
§ 371 (c)(1),
(2), (4) Date: Dec. 15, 2010

(87) PCT Pub. No.: WO2010/000459
PCT Pub. Date: Jan. 7, 2010

(65) Prior Publication Data
US 2011/0092460 A1    Apr. 21, 2011

(30) Foreign Application Priority Data

Jul. 1, 2008   (EP) ..................... 08159396
Dec. 8, 2008   (EP) ..................... 08171005

(51) Int. Cl.
*A01N 43/54*   (2006.01)
*A61K 31/505*  (2006.01)

(52) U.S. Cl.
USPC ........................................ 514/274; 544/317

(58) Field of Classification Search ............ 544/317
See application file for complete search history.

(56) References Cited

U.S. PATENT DOCUMENTS

| | | | |
|---|---|---|---|
| 5,484,801 A | 1/1996 | Al-Razzak et al. | |
| 5,948,436 A | 9/1999 | Al-Razzak et al. | |
| 6,037,157 A | 3/2000 | Norbeck | |

FOREIGN PATENT DOCUMENTS

| | | | |
|---|---|---|---|
| WO | 9414436 A1 | 7/1994 | |
| WO | 9507696 A1 | 3/1995 | |
| WO | 9509614 A1 | 4/1995 | |
| WO | 02100415 A2 | 12/2002 | |
| WO | 2004002999 A2 | 1/2004 | |
| WO | WO 2004002999 A2 * | 1/2004 | |
| WO | 2006021341 A1 | 3/2006 | |
| WO | WO2008043704 A1 | 4/2008 | |

OTHER PUBLICATIONS

International Preliminary Report on Patentability, PCT/PCT/EP2009/004748 (Jan. 5, 2008).*
J.M. Berke et al., 55 Antimicrobial Agents and Chemotherapy, 3812-3820 (2011).*
T.H. Jonkers et al., 53 Journal of Medicinal Chemistry 8150-8160 (2010).*
S. Czernecki et al, 71 Canadian Journal of Chemistry 413-416 (1992).*
Eisuke Murakami et al, Feb. 2007, Mechanism of Activation of B-D-2'Deoxy-2'-Fluoro-2'-C-Methylcytidine and Inhibition of Hepatitis C Virus NS5B RNA Polymerase, Antimicrobial Agents and Chemotherapy, vol. 51, No. 2, pp. 503-509.
Krieger, et al, May 1, 2001, Enhancement of Hepatitis C Virus RNA Replication by Cell Culture, Journal of Virology, 75-10, 4614-1624.
Lohmann, et al., 1999, Replication of Subgenomic Hepatitis C Virus RNAs in a Hepatoma Cell Line, Science, vol. 285, pp. 110-113.
Stanislas Czernecki et al, Jan. 1, 1993, Synthesis of 2'-deocy-2'spirocyclopropyl cytidine as potential inhibitor of ribonucleotide diphosphate reductase, Canadian Journal of Chemistry, vol. 71, p. 413-416.

* cited by examiner

*Primary Examiner* — James O Wilson
*Assistant Examiner* — Alexander R Pagano
(74) *Attorney, Agent, or Firm* — Andrea Jo Kamage

(57) ABSTRACT

Compounds of formula I:

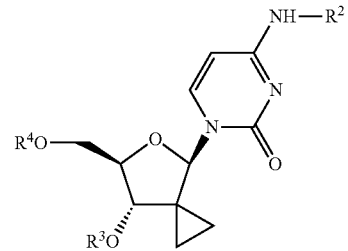

wherein:
$R^2$ is hydrogen or $C_1$-$C_4$alkyl;
$R^3$ and $R^4$ are hydrogen, —C(=O)$R^5$, or —C(=O)CHR$^6$—NH$_2$; or
$R^3$ is hydrogen and $R^4$ is a monophosphate-, diphosphate-, or triphosphate ester; or $R^3$ is hydrogen, —C(=O)CHR$^5$, or —C(=O)CHR$^6$—NH$_2$ and $R^4$ is

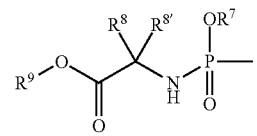

each $R^5$ is hydrogen, $C_1$-$C_6$alkyl, or $C_3$-$C_7$cycloalkyl;
$R^6$ is hydrogen or $C_1$-$C_6$alkyl;
$R^7$ is optionally substituted phenyl; naphthyl; or indolyl;
$R^8$ and $R^{8'}$ are hydrogen, $C_1$-$C_6$alkyl, benzyl; or
$R^8$ and $R^{8'}$ combined form $C_3$-$C_7$cycloalkyl;
$R^9$ is $C_1$-$C_6$alkyl, benzyl, or optionally substituted phenyl;
provided that $R^2$, $R^3$ and $R^4$ are not all hydrogen;
or a pharmaceutically acceptable salt or solvate thereof;
pharmaceutical formulations with the compounds I; the use of compounds I, including the compounds of formula I wherein $R^2$, $R^3$ and $R^4$ are all hydrogen, as HCV inhibitors.

16 Claims, No Drawings

CYCLOPROPYL POLYMERASE INHIBITORS

TECHNICAL FIELD

This invention relates to nucleoside derivatives that are inhibitors of the hepatitis C virus (HCV) as well as their use in the treatment or prophylaxis of HCV.

BACKGROUND OF THE INVENTION

HCV is a single stranded, positive-sense RNA virus belonging to the Flaviviridae family of viruses in the hepacivirus genus. Following initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis, leading to cirrhosis, end-stage liver disease, and HCC (hepatocellular carcinoma), making it the leading cause of liver transplantations.

There are six major HCV genotypes and more than 50 subtypes, which are differently distributed geographically. HCV genotype 1 is the predominant genotype in Europe and in the US. The extensive genetic heterogeneity of HCV has important diagnostic and clinical implications, perhaps explaining difficulties in vaccine development and limited efficacy of current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to end-stage liver disease, existing infections will continue to present a serious medical and economic burden for a very long time.

Current anti-HCV standard of care is based on (pegylated) interferon-alpha (IFN-α) in combination with ribavirin. This combination therapy yields a sustained virologic response in about 50% of patients infected with genotype 1 HCV and about 80% of those infected with genotypes 2 and 3. Beside the limited efficacy on HCV genotype 1, this combination therapy has significant side effects and is poorly tolerated in many patients. Major side effects include influenza-like symptoms, hematologic abnormalities, and neuropsychiatric symptoms. Hence there is a need for more effective, convenient and better-tolerated treatments.

Experience with HIV drugs, in particular with HIV protease inhibitors, has taught that sub-optimal pharmacokinetics and complex dosing regimens quickly result in inadvertent compliance failures. This in turn means that the 24-hour trough concentration (minimum plasma concentration) for the respective drugs in an HIV regime frequently falls below the $IC_{90}$ or $ED_{90}$ threshold for large parts of the day. It is considered that a 24-hour trough level of at least the $IC_{50}$, and more realistically, the $IC_{90}$ or $ED_{90}$, is essential to slow down the development of drug-escape mutants. Achieving the necessary pharmacokinetics and drug metabolism to allow such trough levels provides a stringent challenge to drug design.

The NS5B region of the RNA polygene encodes an RNA dependent RNA polymerase (RdRp), which is essential to viral replication. This enzyme therefore has elicited significant interest among medicinal chemists. Both nucleoside and non-nucleoside inhibitors of NS5B are known. Nucleoside inhibitors can act either as a chain terminator or as a competitive inhibitor, which interferes with nucleotide binding to the polymerase. To function as a chain terminator the nucleoside analog must be taken up by the cell and converted in vivo to a triphosphate. This conversion to the triphosphate is commonly mediated by cellular kinases, which imparts additional structural requirements on a potential nucleoside polymerase inhibitor. In addition, this limits the direct evaluation of nucleosides as inhibitors of HCV replication to cell-based assays capable of in situ phosphorylation.

Several attempts have been made to develop nucleosides as inhibitors of HCV RdRp, but while a handful of compounds have entered clinical development, none have proceeded all the way to registration. Amongst the problems which HCV-targeted nucleosides to date have encountered are toxicity, mutagenicity, lack of selectivity, poor efficacy, poor bioavailability, sub-optimal dosage regimes and ensuing high pill burden, and cost of goods.

Several patents and patent applications as well as scientific publications disclose nucleoside analogs having HCV inhibitory activity. WO 2004/002999 discloses modified 2' and 3'-nucleoside prodrugs for treating flaviviridae infections. WO 2008/043704 discloses 4-amino-1-((2R,3S,4S,5R)-5-azido-4-hydroxy-5-hydroxy-methyl-3-methyl-tetrahydrofuran-2-yl)-1H-pyrimidin-2-one and ester derivatives as HCV polymerase inhibitors. Murakami Eisuke et al. in Antimicrobial Agents and Chemotherapy, American Society for Microbiology, Vol. 51, no. 2, pp. 503-509 (2007) discloses the phosphorylation and the inhibition of HCV NS5B polymerase of β-D-2'-deoxy-2'-fluoro-2'C-methylcytidine and some analogs. None of these compounds has a 2'-spirocyclopropyl substituent.

There is a need for HCV inhibitors that may overcome one or more of the disadvantages of current HCV therapy such as side effects, limited efficacy, the emerging of resistance, and compliance failures, as well as improve sustained viral response.

The present invention concerns HCV inhibiting 4-amino-1-(7-hydroxy-6-hydroxy-methyl-5-oxa-spiro[2.4]hept-4-yl)-1H-pyrimidin-2-ones with useful properties regarding one or more of the following parameters: antiviral efficacy, favorable profile of resistance development, favorable virological profile, a favorable toxicological and genotoxological profile, and favorable pharmacokinetics and pharmacodynamics, and ease of formulation and administration. One such compound, namely 4-amino-1-((4R,6R,7S)-7-hydroxy-6-hydroxymethyl-5-oxa-spiro[2.4]hept-4-yl-)-1H-pyrimidin-2-one, also referred to as 2'-deoxy-2'-spirocyclopropyl cytidine has been described in Can. J. Chem., vol. 71, pp. 413-416, but not as an HCV inhibitor.

Compounds of the invention may also be attractive due to the fact that they lack activity against other viruses, in particular against HIV. HIV infected patients often suffer from co-infections such as HCV. Treatment of such patients with an HCV inhibitor that also inhibits HIV may lead to the emergence of resistant HIV strains.

DESCRIPTION OF THE INVENTION

In one aspect the present invention provides compounds, which can be represented by the formula I:

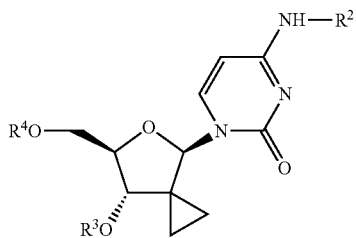

(I)

including any possible stereoisomers thereof, wherein:

$R^2$ is hydrogen or $C_1$-$C_4$alkyl;

$R^3$ and $R^4$ are independently selected from the group consisting of hydrogen, —C(=O)$R^5$, and —C(=O)CHR$^6$—NH$_2$; or $R^3$ is hydrogen and $R^4$ is a monophosphate-, diphosphate-, or triphosphate ester; or $R^3$ is hydrogen, —C(=O)CHR$^5$, or —C(=O)CHR$^6$—NH$_2$ and $R^4$ is a group of formula

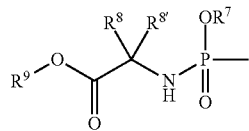

each $R^5$ is independently selected from the group consisting of hydrogen, $C_1$-$C_6$alkyl, and $C_3$-$C_7$cycloalkyl;

$R^6$ is hydrogen or $C_1$-$C_6$alkyl;

$R^7$ is phenyl, optionally substituted with 1, 2 or 3 substituents each independently selected from halo, $C_1$-$C_6$alkyl, $C_3$-$C_6$alkenyl, $C_1$-$C_6$alkoxy, hydroxy, and amino, or $R^7$ is naphthyl; or $R^7$ is indolyl;

$R^8$ is hydrogen, $C_1$-$C_6$alkyl, benzyl;

$R^{8'}$ is hydrogen, $C_1$-$C_6$alkyl, benzyl; or $R^8$ and $R^{8'}$ together with the carbon atom to which they are attached form $C_3$-$C_7$cycloalkyl;

$R^9$ is $C_1$-$C_6$alkyl, benzyl, or phenyl, wherein said phenyl may be optionally substituted with 1, 2 or 3 substituents each independently selected from hydroxy, $C_1$-$C_6$alkoxy, amino, mono- and di$C_1$-$C_6$alkylamino;

provided that $R^2$, $R^3$ and $R^4$ are not all hydrogen;

or a the pharmaceutically acceptable salts or solvates thereof.

In a further aspect, the invention concerns the use of compounds of formula I, as specified herein, including the compound of formula I wherein $R^2$, $R^3$ and $R^4$ are all hydrogen, for inhibiting and treating HCV infection. Alternatively, there is provided the use for the manufacture of a medicament of a compound of formula I, as specified herein, including the compound wherein $R^2$, $R^3$ and $R^4$ are all hydrogen, for inhibiting and treating HCV infection.

The group —NH—C($R^8$)($R^{8'}$)—C(=O)— forms an amino acid residue, which includes natural and non-natural amino acid residues. Of interest are those amino acid residues wherein $R^{8'}$ is hydrogen. Where in the latter instance $R^8$ is other than hydrogen, the configuration at the asymmetric carbon atom bearing $R^8$ may be that of an L-amino acid. This configuration may also be designated as the S-configuration. Examples are alanine (Ala), i.e. where $R^{8'}$ is hydrogen and $R^8$ is methyl; or valine (Val) i.e. where $R^{8'}$ is hydrogen and $R^8$ is isopropyl; leucine (Leu) i.e. where $R^{8'}$ is hydrogen and $R^8$ is —CH$_2$CH(CH$_3$)$_2$; isoleucine (Ile) i.e. where $R^{8'}$ is hydrogen and $R^8$ is —CH(CH$_3$)CH$_2$CH$_3$; and phenylalanine (Phe) i.e. where $R^{8'}$ is hydrogen and $R^8$ is benzyl; in particular L-Ala, L-Val, L-Ile, and L-Phe. An example of an amino acid residue wherein $R^8$ and $R^{8'}$ together with the carbon atom to which they are attached form $C_3$-$C_7$cycloalkyl, is 1,1-cyclopropylamino acid. Where $R^8$ and $R^{8'}$ are both hydrogen, the group —NH—C($R^8$)($R^{8'}$)—C(=O)— forms glycine (Gly).

The group —C(=O)CHR$^6$—NH$_2$ forms an amino acid ester, with an amino acid having no side chain ($R^6$ is hydrogen) or a $C_1$-$C_6$alkyl side chain. Such amino acids comprise glycine ($R^6$ is hydrogen), valine ($R^6$ is isopropyl), leucine ($R^6$ is —CH$_2$CH(CH$_3$)$_2$, or isoleucine ($R^6$ is —CH(CH$_3$)CH$_2$CH$_3$), in particular the L-stereoisomeric forms H-L-Val-, H-L-Leu- or H-L-Ile-.

Subgroups of compounds of formula I are those compounds of formula I, or subgroups of compounds of formula I, as defined herein, wherein $R^2$ is hydrogen.

Subgroups of compounds of formula I are those compounds of formula I, or subgroups of compounds of formula I, as defined herein, wherein $R^3$ is hydrogen.

Subgroups of compounds of formula I are those compounds of formula I, or subgroups of compounds of formula I, as defined herein, wherein $R^4$ is hydrogen.

Subgroups of compounds of formula I are those compounds of formula I, or subgroups of compounds of formula I, as defined herein, wherein one of $R^3$ and $R^4$ is hydrogen and the other of $R^3$ and $R^4$ is selected from acetyl, pivaloyl, and, preferably, isobutyryl; or one of $R^3$ and $R^4$ is hydrogen and the other of $R^3$ and $R^4$ is selected from leucyl, isoleucyl, and, preferably, valyl; or both $R^3$ and $R^4$ are selected from acetyl, pivaloyl, and, preferably, isobutyryl; or both $R^3$ and $R^4$ are selected from leucyl, isoleucyl, and, preferably, valyl. In one embodiment $R^3$ is hydrogen and $R^4$ is as defined above. In another embodiment $R^4$ is hydrogen and $R^3$ is as defined above. Particular subgroups of compounds of formula I are those compounds of formula I, or subgroups of compounds of formula I, as defined herein, wherein $R^3$ and $R^4$ are both isobutyryl (—C(=O)—CH(CH$_3$)$_2$).

Subgroups of compounds of formula I are those compounds of formula I, or subgroups of compounds of formula I, as defined herein, wherein $R^3$ is hydrogen or —C(=O)$R^5$, and $R^4$ is a group of formula

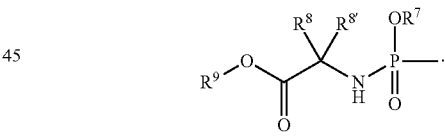

Subgroups of compounds of formula I are those compounds of formula I, or subgroups of compounds of formula I, as defined herein, wherein each $R^5$ is $C_1$-$C_6$alkyl, in particular methyl, isopropyl (1-methylethyl), isobutyl (2-methylpropyl), sec-butyl (1-methylpropyl).

Subgroups of compounds of formula I are those compounds of formula I, or subgroups of compounds of formula I, as defined herein, wherein $R^6$ is hydrogen or $C_1$-$C_4$alkyl, in particular hydrogen, methyl or isobutyl.

Subgroups of compounds of formula I are those compounds of formula I, or subgroups of compounds of formula I, as defined herein, wherein:

(a) $R^7$ is phenyl, optionally substituted with 1 or 2 substituents each independently selected from halo, $C_1$-$C_6$alkyl, $C_3$-$C_6$alkenyl, $C_1$-$C_6$alkoxy, hydroxy, and amino, or $R^7$ is naphthyl; or $R^7$ is indolyl;

(b) $R^7$ is phenyl, optionally substituted with halo, $C_1$-$C_6$alkyl, $C_3$-$C_6$alkenyl, or $C_1$-$C_6$alkoxy, or $R^7$ is naphthyl;

(c) R⁷ is phenyl, optionally substituted with halo or C₁-C₆alkyl, or R⁷ is naphthyl;
(d) R⁷ is phenyl, optionally substituted with halo.

In one embodiment, the group indolyl in the compounds of formula I or any of the subgroups thereof is 5-indolyl.

Subgroups of compounds of formula I are those compounds of formula I, or subgroups of compounds of formula I, as defined herein, wherein R⁸ is hydrogen and R⁸' is methyl or C₁-C₆alkyl, such as isopropyl or isobutyl. Subgroups of compounds of formula I are those compounds of formula I, or subgroups of compounds of formula I, as defined herein, wherein the

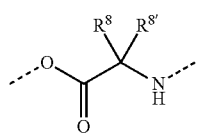

moiety is glycyl, alanyl, or valyl (Gly, Ala, or Val; in particular Gly, L-Ala, or L-Val).

Subgroups of compounds of formula I are those compounds of formula I, or subgroups of compounds of formula I, as defined herein, wherein
(a) R⁹ is C₁-C₆alkyl or benzyl;
(b) R⁹ is C₁-C₆alkyl;
(c) R⁹ is C₁-C₄alkyl; or
(d) R⁹ is methyl, ethyl, or t-butyl.

The compounds of formula I have several centers of chirality, in particular at the carbon atoms 1', 3', and 4'. Although the stereochemistry at these carbon atoms is fixed, the compounds may display at least 75%, preferably at least 90%, such as in excess of 95%, enantiomeric purity at each of the chiral centers. Chirality may also be present in the substituents, such as where R³ and/or R⁴ are —C(=O)CHR⁶—NH₂, with R⁶ other than hydrogen; or such as in the group

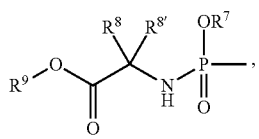

which can have chirality at the R⁸ bearing carbon (where R⁸ and R⁸' are different) and at the phosphorus atom. The phosphorus center can be present as R_P or S_P, or a mixture of such stereoisomers, including racemates. Diastereoisomers resulting from the chiral phosphorus center and a chiral carbon atom may exist as well.

Embodiments of the invention concern the use as HCV inhibitors of the compound denoted 2'-deoxy-2'-spirocyclopropyl cytidine (the compound of formula I wherein R², R³ and R⁴ are all hydrogen); or the compound denoted bis 3',5'-isobutyryl-2'-deoxy-2'-spirocyclopropyl cytidine (the compound of formula I wherein R² is hydrogen and R³ and R⁴ are both —C(=O)R⁵ wherein R⁵ is isopropyl); both in free form or in the form of a pharmaceutically acceptable acid addition salt or a solvate thereof; as inhibitors of HCV or in the treatment or prevention of HCV infection.

One embodiment concerns the compounds designated as compounds 1, 2a, 2b, 2c, 2d, 3, 4, 5, 6 and 7, as mentioned in the examples section hereinafter, in free form. Another embodiment concerns these compounds as well as the pharmaceutically acceptable salts and solvates thereof. A particular embodiment concerns the compound bis 3',5'-isobutyryl-2'-deoxy-2'-spirocyclopropyl cytidine in free form. A further particular embodiment concerns bis 3',5'-isobutyryl-2'-deoxy-2'-spirocyclopropyl cytidine, the pharmaceutically acceptable acid addition salts and solvates thereof.

In a further aspect, the invention provides a compound of formula I or a pharmaceutically acceptable salt, hydrate, or solvate thereof, for use in the treatment or prophylaxis (or the manufacture of a medicament for the treatment or prophylaxis) of HCV infection. Representative HCV genotypes in the context of treatment or prophylaxis in accordance with the invention include genotype 1b (prevalent in Europe) or 1a (prevalent in North America). The invention also provides a method for the treatment or prophylaxis of HCV infection, in particular of the genotype 1a or 1b.

The compounds of formula I are represented as a defined stereoisomer. The absolute configuration of such compounds can be determined using art-known methods such as, for example, X-ray diffraction or NMR and/or implication from start materials of known stereochemistry. Pharmaceutical compositions in accordance with the invention will preferably comprise substantially stereoisomerically pure preparations of the indicated stereoisomer.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl-tartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of formula I can be obtained separately by conventional methods. Appropriate physical separation methods that may advantageously be employed are, for example, selective crystallization and chromato-graphy, e.g. column chromatography.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The pharmaceutically acceptable addition salts comprise the therapeutically active non-toxic acid and base addition salt forms of the compounds of formula I. Of interest are the free (i.e. non-salt) forms of the compounds of formula I, or of any subgroup of compounds of formula I specified herein. As used herein, term "free form" refers to a compound of formula I that is not a salt form or a solvate.

The pharmaceutically acceptable acid addition salts can conveniently be obtained by treating the free form with an appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxy-butanedioic acid), tartaric, citric, methanesulfonic, ethanesulfonic, benzenesulfonic, p-toluenesulfonic, cyclamic, salicylic, p-aminosalicylic, pamoic and the like acids. Conversely, said acid addition salt forms can be converted by treatment with an appropriate base into the free form.

The compounds of formula I containing an acidic proton may also be converted into their pharmaceutically acceptable metal or amine addition salt forms by treatment of the free form with an appropriate organic and inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. Conversely, said metal or amine addition salt forms can be converted into the free form by treatment with an appropriate acid.

The term "solvates" covers any pharmaceutically acceptable solvates that the compounds of formula I as well as the salts thereof, are able to form. Such solvates are for example hydrates, alcoholates, e.g. ethanolates, propanolates, and the like.

Some of the compounds of formula I may also exist in their tautomeric form. For example, tautomeric forms of amide (—C(=O)—NH—) groups are iminoalcohols (—C(OH)=N—), which can become stabilized in rings with aromatic character. Such forms, although not explicitly indicated in the structural formulae represented herein, are intended to be included within the scope of the present invention.

As used herein "$C_1$-$C_4$alkyl" as a group or part of a group defines saturated straight or branched chain hydrocarbon radicals having from 1 to 4 carbon atoms such as for example methyl, ethyl, 1-propyl, 2-propyl, 1-butyl, 2-butyl, 2-methyl-1-propyl, 2-methyl-2-propyl. "$C_1$-$C_6$alkyl" encompasses $C_1$-$C_4$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_1$-$C_6$alkyl is $C_1$-$C_4$alkyl.

"$C_1$-$C_6$alkoxy" means a radical —O—$C_1$-$C_6$alkyl wherein $C_1$-$C_6$alkyl is as defined above. Examples of $C_1$-$C_6$alkoxy are methoxy, ethoxy, n-propoxy, and isopropoxy.

"$C_3$-$C_7$cycloalkyl" includes cyclopropyl, cyclobutyl, cyclopentyl, cyclohexyl and cycloheptyl. A subgroup of these is $C_3$-$C_6$cycloalkyl. Of interest is cyclopropyl.

The term "$C_3$-$C_6$alkenyl" as a group or part of a group defines straight and branched chained hydrocarbon radicals having saturated carbon-carbon bonds and at least one double bond, and having from 3 to 6 carbon atoms, such as, for example, 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst $C_3$-$C_6$alkenyl is $C_3$-$C_4$alkenyl. Of interest amongst $C_3$-$C_6$alkenyl or $C_3$-$C_4$alkenyl are those radicals having one double bond.

The term "halo" is generic to fluoro, chloro, bromo and iodo.

As used herein, the term "(=O)" or "oxo" forms a carbonyl moiety when attached to a carbon atom. It should be noted that an atom can only be substituted with an oxo group when the valency of that atom so permits.

The term "monophosphate, diphosphate or triphosphate ester" refers to groups:

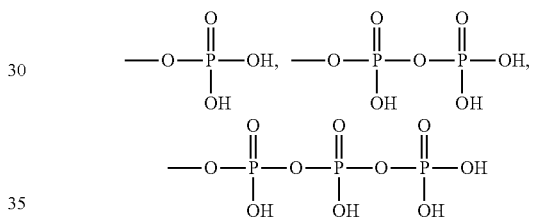

As used herein, the radical positions on any molecular moiety used in the definitions may be anywhere on such a moiety as long as it is chemically stable. When any variable is present more than once in any given moiety, each definition of this variable is independent.

Whenever used herein, the term "compounds of formula I", or "the present compounds" or similar terms, it is meant to include the compounds of formula I, including the possible stereochemically isomeric forms, and their pharmaceutically acceptable salts and solvates.

Preparation Methods

The compounds of formula I wherein $R^3$ and $R^4$ are both hydrogen, herein represented by formula I-a, can be prepared by an uracil to cytosine conversion reaction from a 2'-deoxy-2'-spirocyclopropyl uridine if to the corresponding 2'-deoxy-2'-spirocyclopropyl cytidine 1 g, followed by removal of the protecting groups PG yielding the desired end product I-a. This uracil to cytosine conversion can be carried out by reacting the uracil derivative with $POCl_3$ or a phosphorodichloridate, such as a phenyl or substituted phenyl phosphorodichloridate, e.g. 4-chlorophenyl phosphorodichloridate, and triazole or tetrazole. This reaction can be conducted in a reaction-inert solvent in the presence of a base, for example a halogenated hydrocarbon such as dichloromethane, in the presence of a tertiary amine such as triethylamine. Or a basic solvent such as pyridine can also be used. If desired, the resulting triazole or tetrazole derivatives of formulae

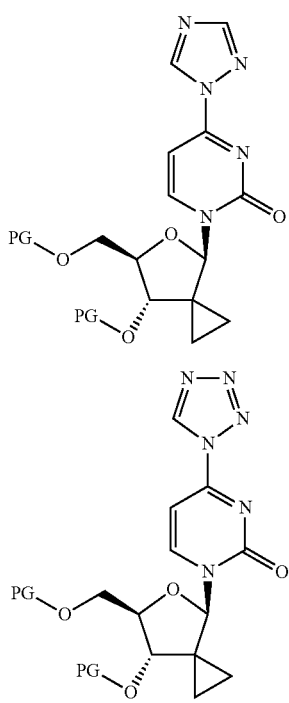

can be isolated and purified. Treatment of the latter with ammonia or $R^2$—$NH_2$ yields the corresponding cytosine derivative 1g. Removal of the PG groups finally leads to the desired end product I. As used herein, PG represents a hydroxy-protecting group, in particular one of the groups mentioned hereinafter.

The intermediates 1f used in the above described conversion are obtained by a cyclopropane ring formation reaction at the exo double bond in intermediates 1d and subsequent removal of the nitrogen protecting group in intermediates 1e. The cyclopropane ring formation involves the addition of diazomethane to the exo double bond, followed by a photochemical rearrangement with the formation of a cyclopropane moiety and expulsion of nitrogen, preferably in the presence of a photsensitizer such as benzophenone. These reactions preferably are conducted in reaction-inert solvents, for example the diazomethane reaction can be done in an ether such as diethylether and the photochemical rearrangement in an aromatic hydrocarbon such as benzene or toluene, or an dipolar aprotic dipolar solvent such as acetonitrile, or mixtures thereof.

Intermediates 1d are obtained by a Wittig reaction from intermediates 1c. In this reaction, the latter are reacted with a methyltriphenylphosphonium halide, preferably the chloride or bromide, in a reaction-inert solvent such as an ether, e.g. diethylether or tetrahydrofuran. The intermediates 1c in turn are derived by an oxidation reaction of the 2'-hydroxy group in intermediates 1b, for example with chromium trioxide in the presence of acetic anhydride in pyridine. Selective protection of the 4' and 5'-hydroxy groups in 1a yields intermediates 1b.

In order to avoid side reactions, the 4' and 5'-hydroxy groups are preferably protected with hydroxy protecting groups PG and the amino (NH) function in the uracil moiety is protected with an amino protecting group $PG^1$. The hydroxy protecting groups PG can be different or the same or combined form a cyclic protecting group. PG for example is a trialkylsilyl group such as trimethylsilyl (TMS), tert-butyldimethylsilyl (TBDMS), or triisopropylsilyl (TIPS). Or the two PG groups combined form a polyalkylated disiloxane-1,3-diyl group such as tetraisopropyldisiloxane-1,3-diyl (TIPDS). These groups can be removed by acid or a fluoride ion (such as NaF or tetra-n-butyl-ammonium fluoride—TBAF). Another hydroxy protecting group, which can also be an amino protecting group, is the trityl group or substituted trityl group, e.g. 4-methoxy-trityl ((4-methoxyphenyl) (bisphenyl)methyl), which is removed under acidic conditions, e.g. by treatment with ethanol/HCl, or with acetic acid.

The amino protecting group $PG^1$ is selected such that it is selectively cleavable toward the PG groups. An amino protecting group that can be used is a benzoyl group. Another such group is the dimethylamino methylene group, which can be introduced using dimethylformamide dimethylacetal. The dimethylamino methylene group is removed under acidic conditions, e.g. by treatment with ethanol/HCl.

The above described reactions are illustrated in the following reaction scheme.

Scheme 1: General synthesis of 2'-deoxy-2'-spirocyclopropyl cytidines

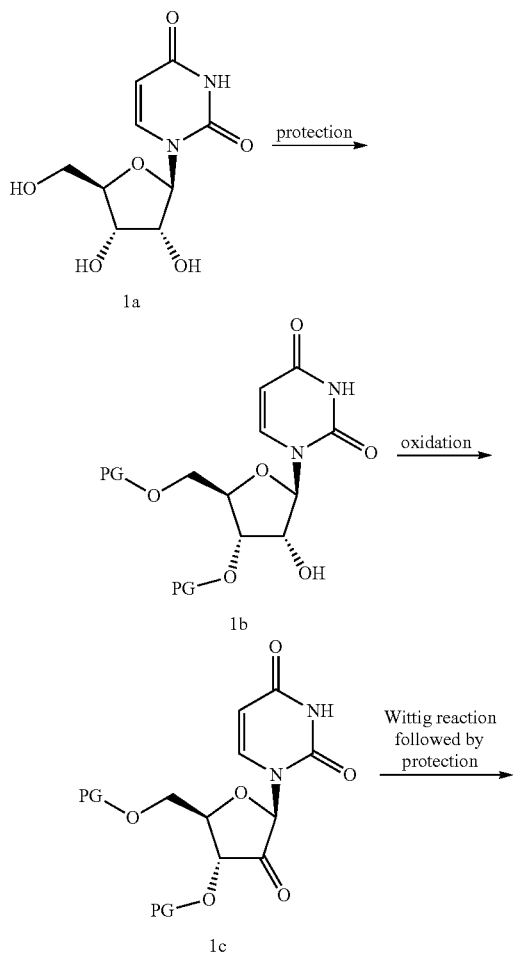

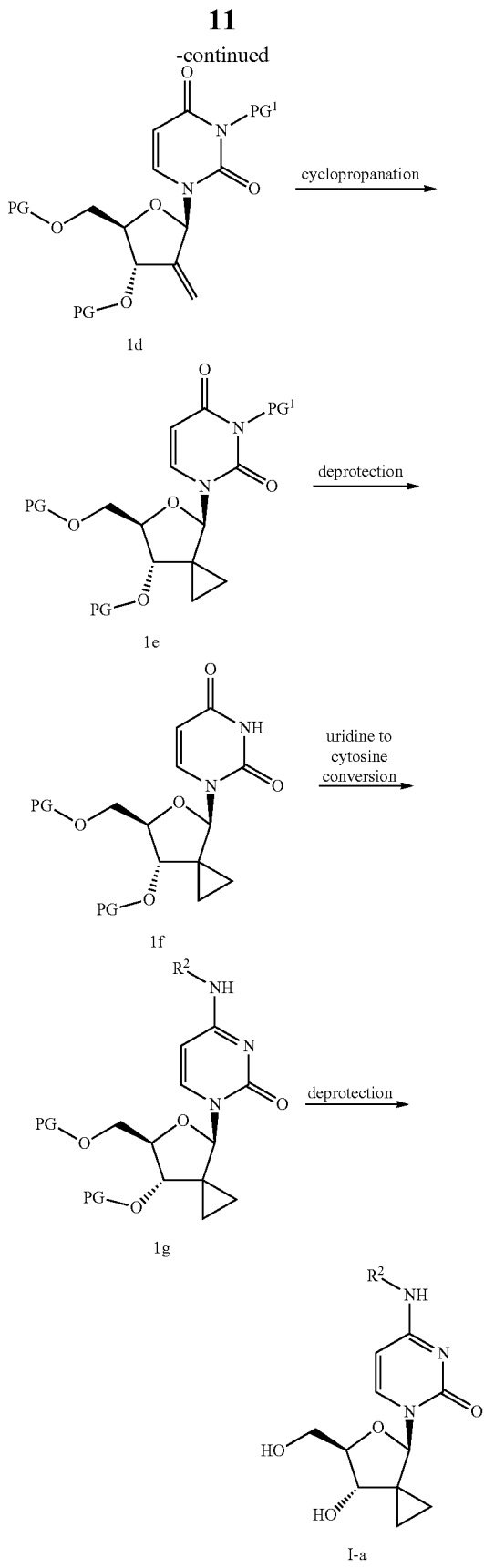

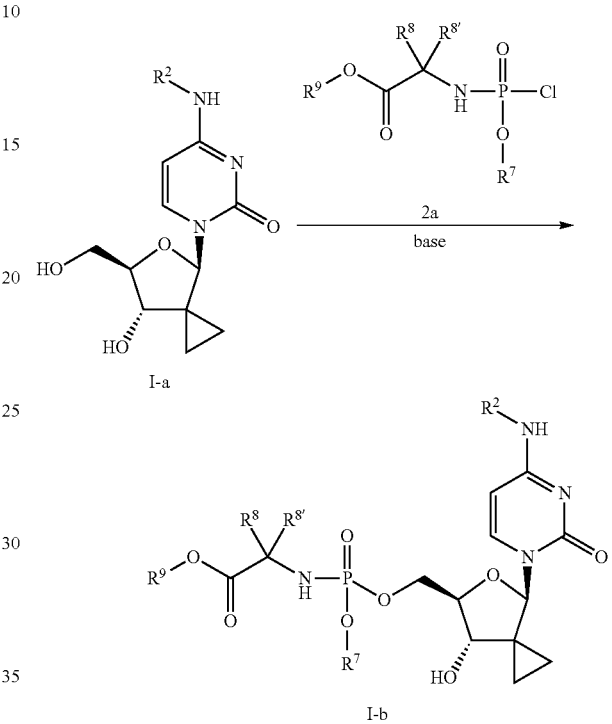

scheme. Compounds I-a are reacted with a phosphorochloridate 2a in the presence of a base yielding phosphoramidates I-b. Solvents that can be used in this reaction comprise ethers, e.g. diethylether or THF, or pyridine, or mixtures thereof. A base such as N-methylimidazole may be added to capture the acid that is formed during the reaction.

The compounds of formula I-a in turn can be converted to phosphoramidates as outlined in the following reaction The synthesis of the mono- or di-esters of I-a is depicted in Scheme 3 herebelow. In this scheme $R^{3a}$ and $R^{4a}$ are independently —C(=O)$R^5$ or —C(=O)CHR$^6$—NH$_2$, or in particular $R^{3a}$ and $R^{4a}$ are independently —C(=O)$R^5$. Where $R^{3a}$ and $R^{4a}$ are independently —C(=O)CHR$^6$—NH$_2$, the amino in the latter group preferably is protected by an amino protecting group such as any of the amino protecting groups PG' described above, and this group can be represented by —C(=O)CHR$^6$—NH-PG$^1$. The amino protecting group can be removed using the appropriate reaction conditions for removal of such group. For example PG$^1$ can be a BOC group and can be removed under acidic conditions. The amino protecting group can be removed at any stage when the free amino group no longer can interfere with subsequent reaction steps, but usually is removed in the last step.

The more reactive 5'-hydroxy group in intermediate 3a can be selectively protected as in intermediate 3b, which in turn is esterified to 3c, followed by a uracil to cytosine conversion to 3d. The latter is deprotected yielding the 3'-monoester I-c. Esterification of the 5'-hydroxy in I-c yields end product I-d. The more reactive 5'-hydroxy can also be selectively esterified introducing a group $R^4$ to yield 3e, and the resulting 5'-ester intermediate can subsequently be esterified with a different acid thereby introducing a group $R^{3a}$, which is as defined above. These esterfication reactions yield di-ester intermediates 3f, which are submitted to a uracil to cytosine conversion, to yield end products I-d. The uracil to cytosine conversion is performed using the procedures described above for the preparation of intermediate 1g.

Scheme 3: Synthesis of mono and di-esters
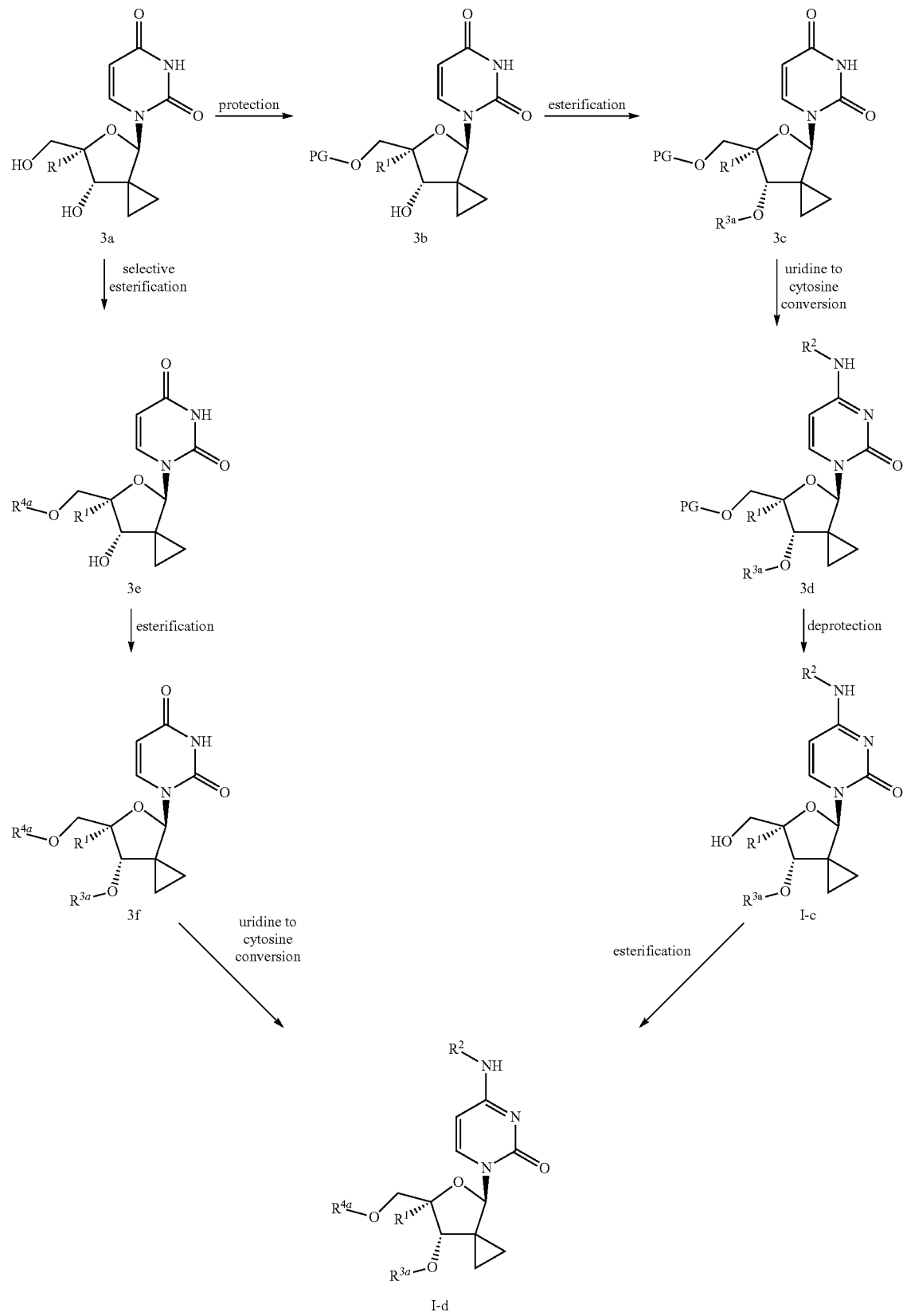

Compounds of formula I wherein $R^{3a}$ is hydrogen and $R^{4a}$ is an ester as specified above, said compounds being represented by I-e, can be prepared by protecting the free hydroxy in intermediate 3b with a hydroxy-protecting group that is selectively cleavable toward the other hydroxy-protecting group resulting in intermediates 4a. The next step then involves removal of the 5'-hydroxy protecting group yielding intermediates 4b, followed by an esterification reaction to intermediates 4c. Subsequent uracil to cytosine conversion yields the corresponding 4'-hydroxy protected cytidine derivatives 4d, which are deprotected to yield 5'-substituted, 4'-unsubstituted derivatives I-e. These reactions are represented in Scheme 4, wherein the group $PG^a$ has the same meaning as PG, but is selected such that PG is selectively cleavable toward the group $PG^a$. For example, PG can be a trityl or 4-methoxytrityl group and $PG^a$ a trialkyl silyl group such as trimethylsilyl or t.butyldimethylsilyl.

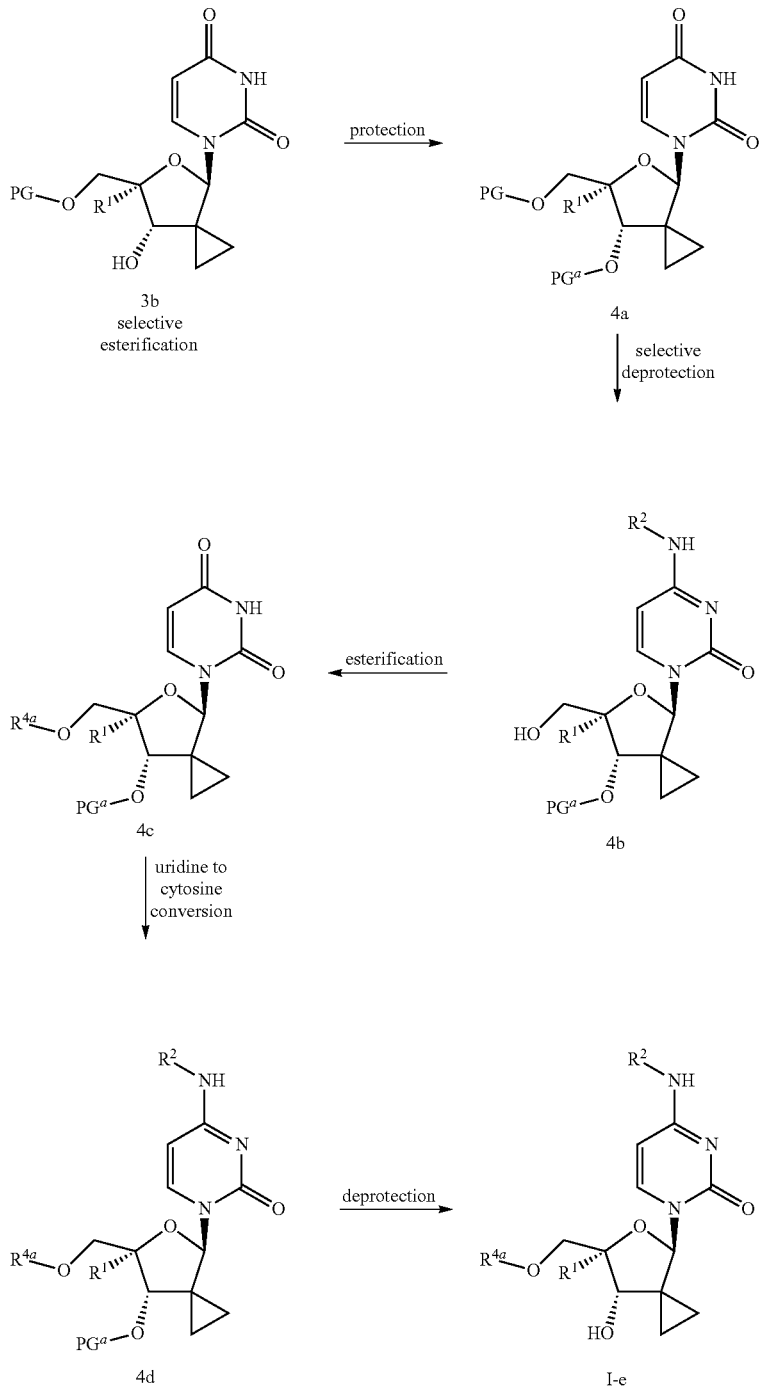

Scheme 4: Synthesis of monoesters

Compounds of formula I wherein $R^{3a}$ and $R^{4a}$ are the same ester groups, hereinafter represented by I-f, can be prepared from compounds 3a by esterifying both hydroxy groups with the same carboxylic acid.

Scheme 5: Synthesis of di-esters

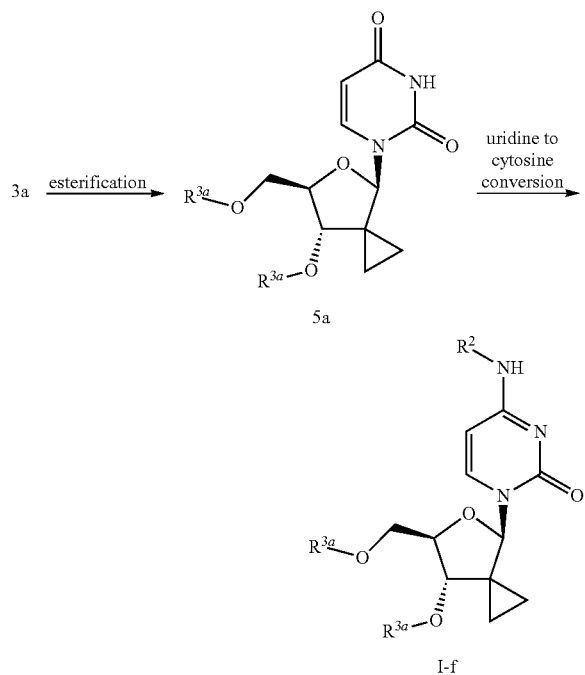

The starting materials 3a can be prepared by removing the hydroxy protecting groups PG in intermediates 1f, which can be prepared as illustrated above in Scheme 1.

The terms "amino protecting" or "N-protecting group" include acyl groups such as formyl, acetyl, propionyl, pivaloyl, t-butylacetyl, 2-chloroacetyl, 2-bromoacetyl, trifluoracetyl, trichloroacetyl, phthalyl, o-nitrophenoxyacetyl, α-chlorobutyryl, benzoyl, 4-chlorobenzoyl, 4-bromo-benzoyl, 4-nitrobenzoyl, and the like; sulfonyl groups such as benzenesulfonyl, p-toluenesulfonyl, and the like; carbamate forming groups such as benzyloxycarbonyl, p-chloro-benzyloxycarbonyl, p-methoxybenzyl-oxycarbonyl, p-nitrobenzyloxycarbonyl, 2-nitrobenzyloxycarbonyl, p-bromobenzyloxycarbonyl, 3,4-dimethoxybenzyloxy-carbonyl, 4-methoxybenzyloxycarbonyl, 2-nitro-4,5-dimethoxybenzyloxycarbonyl, 3,4,5-trimethoxybenzyloxycarbonyl, 1-(p-biphenyl)-1-methylethoxycarbonyl, α,α-dimethyl-3,5-dimethoxybenzyl-oxycarbonyl, benzhydryloxycarbonyl, t-butoxy-carbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxy-carbonyl, phenylthiocarbonyl, and the like; alkyl groups such as benzyl, triphenylmethyl, benzyloxymethyl and the like; and silyl groups such as trimethylsilyl and the like.

Hydroxy-protecting groups include ethers such as methyl, substituted methyl ethers such as methoxymethyl, methylthiomethyl, benzyloxymethyl, t-butoxymethyl, 2-methoxyethoxymethyl and the like; silyl ethers such as trimethylsilyl (TMS), t-butyldimethylsilyl (TBDMS) tribenzylsilyl, triphenylsilyl, t-butyldiphenylsilyl, triisopropyl silyl and the like; substituted ethyl ethers such as 1-ethoxymethyl, 1-methyl-1-methoxyethyl; t-butyl, allyl, benzyl, p-methoxybenzyl, diphenylmethyl, trityl, and the like. Ester hydroxy protecting groups include esters such as formate, benzylformate, chloroacetate, methoxyacetate, phenoxyacetate, pivaloate, adamantoate, mesitoate, benzoate and the like.

In a further aspect, the present invention concerns a pharmaceutical composition comprising a therapeutically effective amount of a compound of formula I, as specified herein, and a pharmaceutically acceptable carrier. A therapeutically effective amount in this context is an amount sufficient to act in a prophylactic way against, or to stabilize or to reduce viral infection, particularly HCV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula I, as specified herein.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration-enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula I show activity against HCV and can be used in the treatment and prophylaxis of HCV infection or diseases associated with HCV. The latter include progressive liver fibrosis, inflammation and necrosis leading to cirrhosis, end-stage liver disease, and HCC. Compounds of this invention moreover may be active against mutated strains of HCV. Additionally, compounds of this invention may show a favorable pharmacokinetic profile and may have attractive properties in terms of bioavailability, including an acceptable half-life, AUC (area under the curve) and peak values and lack unfavorable phenomena such as insufficient quick onset and tissue retention.

Compounds of the invention are also attractive due to their low toxicity and favorable selectivity index as can be demonstrated, for example, in a cellular toxicity test. Compounds of the invention moreover lack activity against other viruses, in particular against HIV. Usage of drugs with a dual or multiple antiviral effect in co-infected patients may lead to suboptimal dosing against the other virus, which in turn can lead to the emergence of resistant viral strains.

The in vitro antiviral activity against HCV of the compounds of formula I can be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula I, including any possible stereoisomers, the pharmaceutically acceptable addition salts or solvates thereof, are useful in the treatment of warm-blooded animals, in particular humans, infected with HCV, and for the prophylaxis of HCV infections in warm-blooded animals, in particular humans. The present invention furthermore relates to a method of treating a warm-blooded animal, in particular a human, infected with HCV, or being at risk of becoming infected with HCV, said method comprising the administration of an anti-HCV effective amount of a compound of formula I, as specified herein.

The compounds of the present invention may therefore be used as a medicine, in particular as an anti-HCV medicine or as an HCV-inhibitory medicine. The present invention also relates to the use of the compounds in the manufacture of a medicament for the treatment or the prevention of HCV infection. Said use as a medicine or method of treatment comprises the systemic administration to HCV infected subjects, or to subjects susceptible to HCV infection, of an amount of a compound of formula I, as specified herein, effective to combat the conditions associated with HCV infection.

In general it is contemplated that an antiviral effective daily amount would be from about 0.01 to about 700 mg/kg, or about 0.5 to about 400 mg/kg, or about 1 to about 250 mg/kg, or about 2 to about 200 mg/kg, or about 10 to about 150 mg/kg body weight. It may be appropriate to administer the required dose as two, three, four or more sub-doses at appropriate intervals throughout the day. Said sub-doses may be formulated as unit dosage forms, for example, containing about 1 to about 5000 mg, or about 50 to about 3000 mg, or about 100 to about 1000 mg, or about 200 to about 600 mg, or about 100 to about 400 mg of active ingredient per unit dosage form.

The invention also relates to a combination of a compound of formula I, a pharmaceutically acceptable salt or solvate thereof, and another antiviral compound, in particular another anti-HCV compound. The term "combination" may relate to a product containing (a) a compound of formula I, as specified above, and (b) optionally another anti-HCV compound, as a combined preparation for simultaneous, separate or sequential use in treatment of HCV infections.

Anti-HCV compounds that can be used in such combinations include HCV polymerase inhibitors, HCV protease inhibitors, inhibitors of other targets in the HCV life cycle, and an immunomodulatory agents, and combinations thereof. HCV polymerase inhibitors include, NM283 (valopicitabine), R803, JTK-109, JTK-003, HCV-371, HCV-086, HCV-796 and R-1479, R-7128, MK-0608, VCH-759, PF-868554, GS9190, XTL-2125, NM-107, GSK625433, R-1626, BILB-1941, ANA-598, IDX-184, IDX-375, MK-3281, MK-1220, ABT-333, PSI-7851, PSI-6130, VCH-916. Inhibitors of HCV proteases (NS2-NS3 inhibitors and NS3-NS4A inhibitors) include BILN-2061, VX-950 (telaprevir), GS-9132 (ACH-806), SCH-503034 (boceprevir), TMC435350 (also referred to as TMC435), TMC493706, ITMN-191, MK-7009, BI-12202, BILN-2065, BI-201335, BMS-605339, R-7227, VX-500, BMS650032, VBY-376, VX-813, SCH-6, PHX-1766, ACH-1625, IDX-136, IDX-316. An example of an HCV NS5A inhibitor is BMS790052, A-831, A-689, NIM-811 and DEBIO-025 are examples of NS5B cyclophilin inhibitors.

Inhibitors of other targets in the HCV life cycle, including NS3 helicase; metallo-protease inhibitors; antisense oligonucleotide inhibitors, such as ISIS-14803 and AVI-4065; siRNA's such as SIRPLEX-140-N; vector-encoded short hairpin RNA (shRNA); DNAzymes; HCV specific ribozymes such as heptazyme, RPI.13919; entry inhibitors such as HepeX-C, HuMax-HepC; alpha glucosidase inhibitors such as celgosivir, UT-231B and the like; KPE-02003002; and BIVN 401.

Immunomodulatory agents include, natural and recombinant interferon isoform compounds, including α-interferon, β-interferon, γ-interferon, and ω-interferon, such as Intron A®, Roferon-A®, Canferon-A300®, Advaferon®, Infergen®, Humoferon®, Sumiferon MP®, Alfaferone®, IFN-Beta®, and Feron®; polyethylene glycol derivatized (pegylated) interferon compounds, such as PEG interferon-α-2a (Pegasys®), PEG Interferon-α-2b (PEG-Intron®), and pegylated IFN-α-con1; long acting formulations and derivatizations of interferon compounds such as the albumin-fused interferon albuferon α; compounds that stimulate the synthesis of interferon in cells, such as resiquimod; interleukins; compounds that enhance the development of type 1 helper T cell response, such as SCV-07; TOLL-like receptor agonists such as CpG-10101 (actilon), and isatoribine; thymosin α-1; ANA-245; ANA-246; histamine dihydrochloride; propagermanium; tetrachlorodecaoxide; ampligen; IMP-321; KRN-7000; antibodies, such as civacir and XTL-6865; and prophylactic and therapeutic vaccines such as InnoVac C and HCV E1E2/MF59.

Other antiviral agents include, ribavirin, amantadine, viramidine, nitazoxanide; telbivudine; NOV-205; taribavirin; inhibitors of internal ribosome entry; broad-spectrum viral inhibitors, such as IMPDH inhibitors, and mycophenolic acid and derivatives thereof, and including, but not limited to, VX-497 (merimepodib), VX-148, and/or VX-944); or combinations of any of the above.

Particular agents for use in said combinations include interferon-α (IFN-α), pegylated interferon-α or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

In another aspect there are provided combinations of a compound of formula I as specified herein and an anti-HIV compound. The latter preferably are those HIV inhibitors that have a positive effect on drug metabolism and/or pharmacokinetics that improve bioavailability. An example of such an HIV inhibitor is ritonavir. As such, this invention further provides a combination comprising (a) a compound of formula I or a pharmaceutically acceptable salt or solvate thereof; and (b) ritonavir or a pharmaceutically acceptable salt thereof. The compound ritonavir, its pharmaceutically acceptable salts, and methods for its preparation are described in WO 94/14436. U.S. Pat. No. 6,037,157, and references cited therein: U.S. Pat. No. 5,484,801, U.S. Ser. No. 08/402,690, WO 95/07696, and WO 95/09614, disclose preferred dosage forms of ritonavir.

The invention also concerns a process for preparing a combination as described herein, comprising the step of combining a compound of formula I, as specified above, and another agent, such as an antiviral, including an anti-HCV or anti-HIV agent, in particular those mentioned above.

The said combinations may find use in the manufacture of a medicament for treating HCV infection in a mammal infected therewith, said combination in particular comprising a compound of formula I, as specified above and interferon-α (IFN-α), pegylated interferon-α, or ribavirin. Or the invention provides a method of treating a mammal, in particular a human, infected with HCV comprising the administration to said mammal of an effective amount of a combination as specified herein. In particular, said treating comprises the systemic administration of the said combination, and an effective amount is such amount that is effective in treating the clinical conditions associated with HCV infection.

In one embodiment the above-mentioned combinations are formulated in the form of a pharmaceutical composition that includes the active ingredients described above and a carrier, as described above. Each of the active ingredients may be formulated separately and the formulations may be co-administered, or one formulation containing both and if desired further active ingredients may be provided. In the former instance, the combinations may also be formulated as a combined preparation for simultaneous, separate or sequential use in HCV therapy. The said composition may take any of the forms described above. In one embodiment, both ingredients are formulated in one dosage form such as a fixed dosage combination. In a particular embodiment, the present invention provides a pharmaceutical composition comprising (a) a therapeutically effective amount of a compound of formula I, including a possible stereoisomeric form thereof, or a pharmaceutically acceptable salt thereof, or a pharmaceutically acceptable solvate thereof, and (b) a therapeutically effective amount of ritonavir or a pharmaceutically acceptable salt thereof, and (c) a carrier.

The individual components of the combinations of the present invention can be administered separately at different times during the course of therapy or concurrently in divided or single combination forms. The present invention is meant to embrace all such regimes of simultaneous or alternating treatment and the term "administering" is to be interpreted accordingly. In a preferred embodiment, the separate dosage forms are administered simultaneously.

In one embodiment, the combinations of the present invention contain an amount of ritonavir, or a pharmaceutically acceptable salt thereof, that is sufficient to clinically improve the bioavailability of the compound of formula I relative to the bioavailability when said compound of formula I is administered alone. Or, the combinations of the present invention contains an amount of ritonavir, or a pharmaceutically acceptable salt thereof, which is sufficient to increase at least one of the pharmacokinetic variables of the compound of formula I selected from $t_{1/2}$, $C_{min}$, $C_{max}$, $C_{ss}$, AUC at 12 hours, or AUC at 24 hours, relative to said at least one pharmacokinetic variable when the compound of formula I is administered alone.

The combinations of this invention can be administered to humans in dosage ranges specific for each component comprised in said combinations, e.g. the compound of formula I as specified above, and ritonavir or a pharmaceutically acceptable salt, may have dosage levels in the range of 0.02 to 5.0 g/day. The weight ratio of the compound of formula I to ritonavir may be in the range of from about 30:1 to about 1:15, or about 15:1 to about 1:10, or about 15:1 to about 1:1, or about 10:1 to about 1:1, or about 8:1 to about 1:1, or about 5:1 to about 1:1, or about 3:1 to about 1:1, or about 2:1 to 1:1. The compound formula I and ritonavir may be co-administered once or twice a day, preferably orally, wherein the amount of the compound of formula I per dose is as described above; and the amount of ritonavir per dose is from 1 to about 2500 mg, or about 50 to about 1500 mg, or about 100 to about 800 mg, or about 100 to about 400 mg, or 40 to about 100 mg of ritonavir.

All references cited herein are incorporated by reference.
EXAMPLES
In the following examples, the compound names were generated by Chemdraw Ultra™ software, Cambridgesoft, version 9.0.7.
Example 1
4-Amino-1-(7-hydroxy-6-hydroxymethyl-5-oxa-spiro[2.4]hept-4-yl)-1H-pyrimidin-2-one (1)
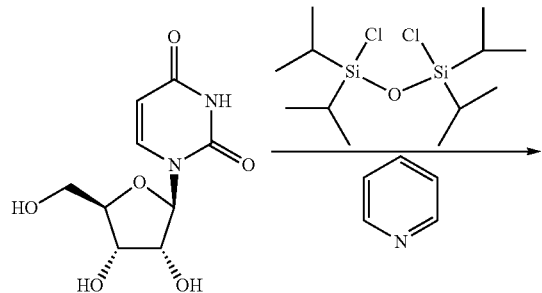
(I-1)
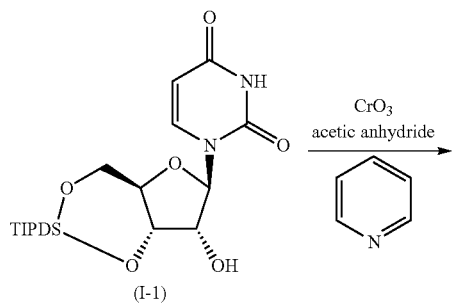
(I-2)
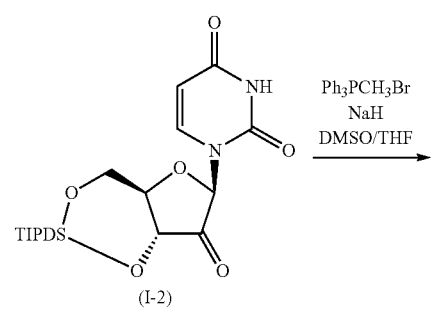
(I-3)
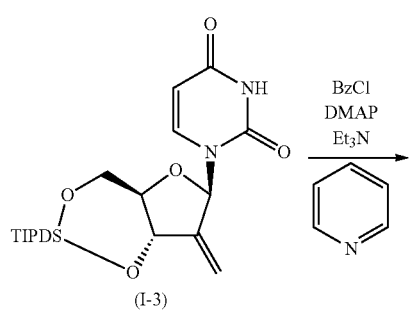
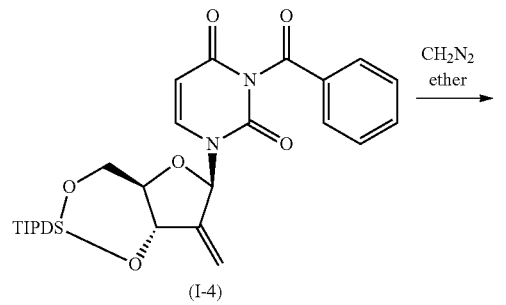
(I-4)
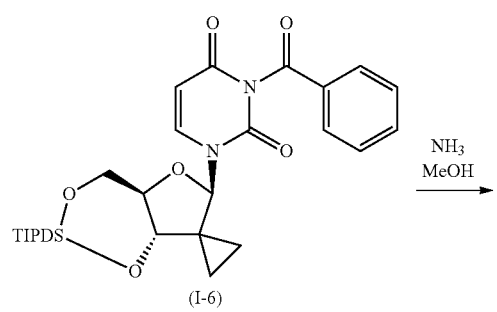
(I-5)
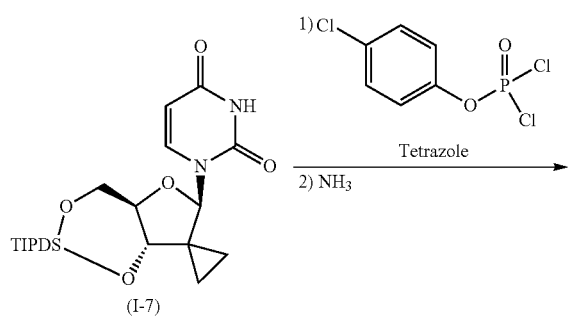
(I-6)
(I-7)
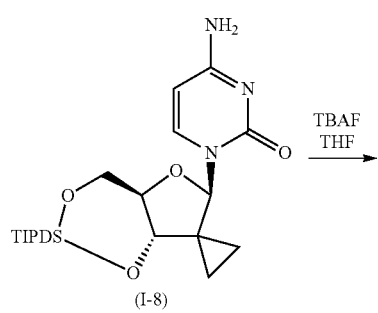
(I-8)

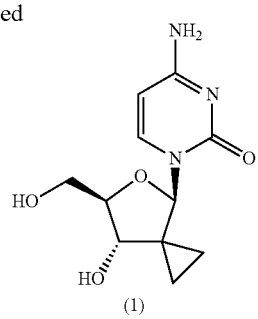

(1)

Step 1: 1-((6aR,8R,9R,9aS)-9-hydroxy-2,2,4,4-tetraisopropyl-6a,8,9,9a-tetrahydro-6H-furo[3,2-f][1,3,5,2,4]trioxadisilocin-8-yl)pyrimidine-2,4(1H,3H)-dione (1-1)

A mixture of D-uridine (20 g) and 1,3-dichloro-1,1,3,3-tetraisopropyldisiloxane (1.018 eq) in pyridine (300 mL) was stirred at room temperature for 64 hours. Pyridine was removed in vacuo (30° C.). The residue was redissolved in 100 mL CH$_2$Cl$_2$, washed with water (3×75 mL), dried with anhydrous MgSO$_4$ and filtered. The filtrate was evaporated to dryness and used as such in the next reaction. LC-MS: Rt: 3.16 min, m/z: 487 (M+H)$^+$.

Step 2: 1-((6aR,8R,9aR)-2,2,4,4-tetraisopropyl-9-oxotetrahydro-6H-furo[3,2-f][1,3,5,2,4]trioxadisilocin-8-yl)pyrimidine-2,4(1H,3H)-dione (I-2)

Intermediate I-1 (19.93 g) was dissolved in 200 mL CH$_2$Cl$_2$, pyridine (1 eq) and acetic anhydride (2.91 eq) were added followed by CrO$_3$ (2.75 eq). The mixture was stirred at room temperature and after 30 minutes a gentle reflux was observed. After stirring for 90 minutes, LC-MS indicated that reaction product I-2 was formed (50%) and starting material I-1 left (50%). Additional stirring for 2 hours resulted in 55% of product I-2 and 45% of I-1 remaining Another 10 mL pyridine, 5 mL acetic acid anhydride and 5 grams of CrO$_3$ were added and the mixture was stirred further at room temperature overnight. LC-MS indicated little progress. The dark brown solution was poured into 1300 mL ethyl acetate and the residue filtered through a pad of dicalite. The precipitate was washed with additional ethyl acetate. The combined filtrates were evaporated to dryness. Intermediate I-2 was purified by column chromatography using CH$_2$Cl$_2$ to CH$_2$Cl$_2$/ethyl acetate 1:1. Thin layer chromatography (TLC) indicated two spots. Intermediate I-2 was therefore repurified by column chromatography using heptane to heptane/aceton 7:3. Fractions containing the product were collected and evaporated resulting in 8.5 grams of a white solid (1-2) LC-MS: Rt: 3.31 min, m/z: 485 (M+H)$^+$, note: the hydrate of the ketone is also observed: LC-MS: Rt: 3.20 min, m/z: 503 (M+H)$^+$.

Step 3: 1-((6aR,8R,9aS)-2,2,4,4-tetraisopropyl-9-methylenetetrahydro-6H-furo[3,2-f][1,3,5,2,4]trioxadisilocin-8-yl)pyrimidine-2,4(1H,3H)-dione (I-3)

NaH (0.897 g) was suspended in 15 mL dry dimethyl sulfoxide (DMSO) and was heated to 65° C. for 1.5 hours under Ar. Methyltriphenylphosphonium bromide (12.84 g) was added with stirring followed by 30 mL dry DMSO and 15 mL dry tetrahydrofuran (THF). The mixture was stirred at room temperature for 1.5 hours. A yellow/orange mixture was formed. Then intermediate I-2 (6.97 g), dissolved in 20 mL dry THF, was added dropwise via a syringe, and the whole was stirred during 1.5 hours at room temperature and then at 50° C. for 1 hour. The mixture was then cooled to room temperature. The precipitate was filtered off over a plug of dicalite, the filtrate was concentrated (to remove THF) and the residue was partitioned between CHCl$_3$ and water (300 mL each). The organic layer was separated and the aqueous layer re-extracted with CHCl$_3$. The combined layers were filtered over a plug of dicalite and concentrated. The product was purified by column chromatography using CH$_2$Cl$_2$ to CH$_2$Cl$_2$/ethyl acetate 7:3 as eluent. Evaporation resulted in 2.97 g of intermediate I-3 as a white solid. LC-MS: Rt: 3.56 min, m/z: 483 (M+H)$^+$.

Step 4: 3-benzoyl-1-((6aR,8R,9aS)-2,2,4,4-tetraisopropyl-9-methylenetetrahydro-6H-furo[3,2-f][1,3,5,2,4]trioxadisilocin-8-yl)pyrimidine-2,4(1H,3H)-dione (I-4)

Intermediate I-3 (2.4 g) was evaporated twice with 20 mL dry pyridine. Then it was redissolved in 30 mL dry pyridine. Di-isopropylethylamine (3 eq) was added followed by benzoylchloride (1.5 eq). The mixture was stirred for 2 hours at room temperature. Pyridine was evaporated in vacuo below 30° C. and 150 mL CH$_2$Cl$_2$ was added. The resulting mixture was washed two times with 50 mL saturated NaHCO$_3$. The organic layer was dried on MgSO$_4$, filtrated and evaporated, and the residue was dried in vacuo for 64 hours. Intermediate I-4 was purified by column chromatography using CH$_2$Cl$_2$ to CH$_2$Cl$_2$/ethyl acetate 8:2 as eluent. After evaporation, 2.89 g of I-4 was obtained as a white foam. LC-MS: Rt: 3.79 min, m/z: 587 (M+H)$^+$.

Step 5: 3-benzoyl-1-((3'R,6aR,8R,9aS)-2,2,4,4-tetraisopropyl-4',5',6,6a,8,9a-hexahydrospiro[furo[3,2-f][1,3,5,2,4]trioxadisilocine-9,3'-pyrazole]-8-yl)pyrimidine-2,4(1H,3H)-dione and its epimer 3-benzoyl-1-((3'S,6aR,8R,9aS)-2,2,4,4-tetraisopropyl-4',5',6,6a,8,9a-hexahydrospiro[furo[3,2-f][1,3,5,2,4]trioxadisilocine-9,3'-pyrazole]-8-yl)pyrimidine-2,4(1H,3H)-dione (I-5)

Diazomethane, generated from N-methyl-N-nitroso-p-toluenesulfonamide (DIAZALD) (4.862 g), and KOH (2.9 g) in diethylether and 2-(2-ethoxyethoxy)ethanol, was distilled into a stirring solution of I-4 (1.072 g) in diethylether (20 mL) that was cooled in an ice-water bath. When distillation was complete, the yellow solution was stirred at room temperature until TLC or LC-MS showed completion of the reaction. The mixture was evaporated to dryness resulting in 1.149 g white foam. LC-MS indicated a 3:1 mixture of epimers (I-5) that was used as such in the next reaction. LC-MS: Rt: 3.67 & 3.68 min, m/z: 629 (M+H)$^+$.

Step 6: 3-benzoyl-1-((6a'R,8'R,9a'S)-2',2',4',4'-tetraisopropylhexahydrospiro[cyclo-propane-1,9'-furo[3,2-f][1,3,5,2,4]trioxadisilocine]-8'-yl)pyrimidine-2,4(1H,3H)-dione (I-6)

A mixture of intermediate I-5 (250 mg) and benzophenone (1 eq) dissolved in 5 mL dry benzene/CH$_3$CN 1:1 was stirred at room temperature under Ar. The mixture was irradiated with a halogen lamp of 150 W until LC-MS showed complete conversion of the starting material. The mixture was evaporated to dryness and intermediate I-6 was purified by column chromatography using CH$_2$Cl$_2$ as the eluent. After evaporation of the pure fractions, I-6 was obtained as a clear oil (150 mg). LC-MS: Rt: 3.91 min, m/z: 601 (M+H)$^+$.

Step 7: 1-((6a'R,8'R,9a'S)-2',2',4',4'-tetraisopropyl-hexahydrospiro[cyclopropane-1,9'-furo[3,2-f][1,3,5,2,4]trioxadisilocine]-8'-yl)pyrimidine-2,4(1H,3H)-dione (I-7)

Intermediate I-6 (150 mg) was dissolved in 3 mL CH$_2$Cl$_2$ and 10 mL NH$_3$/methanol was added. The mixture was stirred for 1 hour, evaporated to dryness, and purified by column chromatography using CH$_2$Cl$_2$ to CH$_2$Cl$_2$/ethyl acetate 9:1 as the eluent. After evaporation, a colorless oil was obtained, which after trituration with diethylether and evaporation resulted into 87 mg of intermediate I-7 as a white foam. LC-MS: Rt: 3.66 min, m/z: 497 (M+H)$^+$.

Step 8: 4-amino-1-((6a'R,8'R,9a'S)-2',2',4',4'-tetraisopropylhexahydrospiro[cyclo-propane-1,9'-furo[3,2-f][1,3,5,2,4]trioxadisilocine]-8'-yl)pyrimidin-2(1H)-one (I-8)

A solution of I-7 (1.0 g) was dissolved in 20 mL dry pyridine and the solution was cooled in an ice-bath. 4-Chlorophenyl phosphorodichloridate (1.5 eq) was added dropwise and the solution was stirred cold for 5 minutes. Then tetrazole (3 eq, 0.45 M solution in CH$_3$CN) was added dropwise. The ice-bath was removed and the reaction allowed proceeding until LC-MS showed no further progress. Another 1 eq of 4-chlorophenyl phosphorodichloridate was added and the mixture was stirred further at room temperature for 3 hours. LC-MS indicated that no starting material was left. The mixture was evaporated to dryness (<40° C.) and the residue was taken into CH$_2$Cl$_2$ (75 mL) and washed twice with saturated NaHCO$_3$. The organic phase was dried with Na$_2$SO$_4$, filtered and evaporated. The residue of the previous reaction was dissolved in 25 mL NH$_3$ solution in dioxane (0.5 M). Additional NH$_3$ in dioxane was added at regular intervals until the reaction was complete as judged by LC-MS. When finished, the mixture was evaporated to dryness. The intermediate I-8 was purified by column chromatography using CH$_2$Cl$_2$ to CH$_2$Cl$_2$/methanol 9:1 as the eluent. After evaporation, I-8 was obtained as a yellow to orange sticky solid (840 mg). LC-MS: Rt: 3.42 min, m/z: 496 (M+H)$^+$.

Step 9: 4-amino-1-(7-hydroxy-6-hydroxymethyl-5-oxa-spiro[2.4]hept-4-yl)-1H-pyrimidin-2-one (1)

Intermediate I-8 (840 mg) was dissolved in 25 mL THF. Tetra-n-butylammonium fluoride (TBAF; 2 eq) was added. The mixture was stirred at room temperature for 1 hour and then evaporated in vacuo. The compound was purified twice by column chromatography using CHCl$_3$/methanol 9:1 to CHCl$_3$/methanol 3:1 as the eluent. After evaporation of the product containing fractions, compound 1 (300 mg) was obtained as a white solid. LC-MS: Rt: 1.25 min m/z: 254 (M+H)$^+$. $^1$H NMR (400 MHz, DMSO-d$_6$) δ ppm 0.31-0.59 (m, 3H), 0.93-1.02 (m, 1H), 3.51-3.65 (m, 1H), 3.71 (d, J=4.89 Hz, 2H), 3.97 (t, J=5.87 Hz, 1H), 4.98 (t, J=4.99 Hz, 1H), 5.12 (d, J=5.87 Hz, 1H), 5.72 (d, J=7.43 Hz, 1H), 6.01 (s, 1H), 7.13 (br. s., 2H), 7.77 (d, J=7.24 Hz, 1H).

Example 2

(2S)-benzyl 2-((((4R,6R,7S)-4-(4-amino-2-oxopyrimidin-1(2H)-yl)-7-hydroxy-5-oxaspiro[2.4]heptan-6-yl)methoxy)((phenoxy)phosphoryl)amino)propanoate (2a)

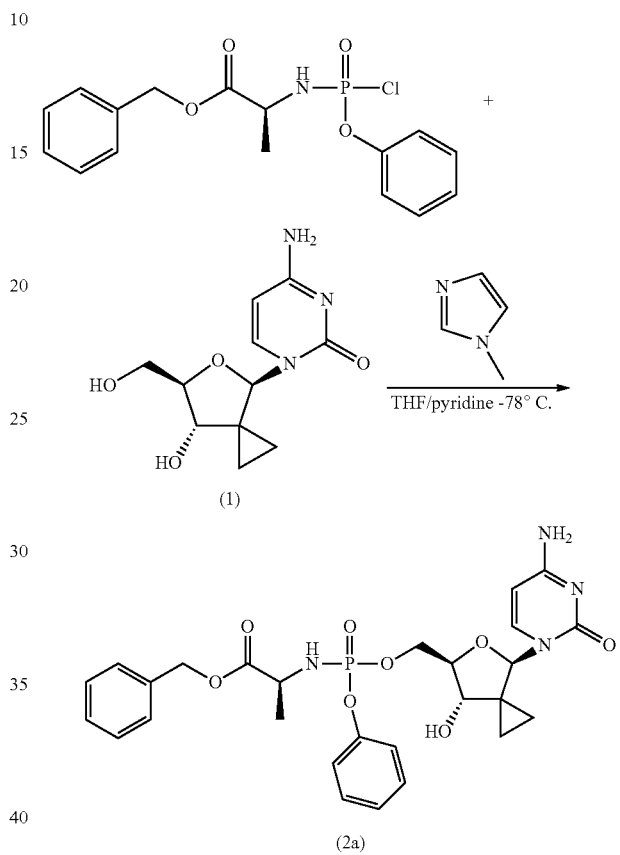

Compound 1 (100 mg) was dissolved in dry THF/pyridine together with (2S)-benzyl 2-(chloro(phenoxy)phosphorylamino)propanoate (279 mg, 2.0 eq). The mixture was cooled to −78° C. N-methylimidazole (NMI) (259 mg, 8 eq) was added and this mixture was stirred for 15 minutes at −78° C. and then stirred at RT overnight. The resulting mixture was evaporated to dryness. 10 mL CH$_2$Cl$_2$ added and the residue washed with 10 mL 0.5N HCl. The organic layer was separated and washed with 10 mL water, dried on Na$_2$SO$_4$, filtered and evaporated. The compound was purified by silica gel chromatography using CH$_2$Cl$_2$ to CH$_2$Cl$_2$/MeOH 9-1 as the eluent. (Rf=0.2 in this eluent). A yellow solid was obtained, which was repurified using column chromatography using EtOAc to EtOAc/MeOH 8-2 as the eluent. After evaporation and drying overnight in vacuo, 80 mg (33.4%) of 2a was obtained (mixture of diastereomers). LC-MS: Rt: 3.37 min m/z: 569 (M−H)$^-$. $^1$H NMR (400 MHz, DMSO-d$_6$) δ ppm 0.31-0.41 (m, 1H), 0.43-0.58 (m, 2H), 0.95-1.06 (m, 1H), 1.20-1.31 (m, 3H), 3.82-4.01 (m, 3H), 4.09-4.23 (m, 1H), 4.23-4.36 (m, 1H), 4.98-5.15 (m, 2H), 5.29-5.39 (m, 1H), 5.70 (d, J=7.43 Hz, 1H), 6.07 (s, 1H), 6.13 (dd, J=12.81, 10.47 Hz, 1H), 7.08-7.25 (m, 6H), 7.29-7.39 (m, 6H), 7.54 (d, 1H).

The following compounds were made in a similar way:

(2S)-benzyl 2-((((4R,6R,7S)-4-(4-amino-2-oxopyrimidin-1(2H)-yl)-7-hydroxy-5-oxaspiro[2.4]heptan-6-yl)methoxy)(4-chlorophenoxy)phosphorylamino)propanoate (2b)

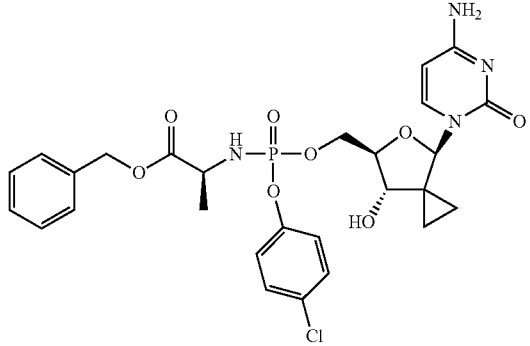

(2b)

LC-MS: Rt: 3.65 min m/z: 603 (M−H)⁻. ¹H NMR (400 MHz, DMSO-d₆) δ ppm 0.30-0.43 (m, 1H), 0.44-0.60 (m, 2H), 0.95-1.06 (m, 1H), 1.20-1.31 (m, 3H), 3.84-4.01 (m, 3H), 4.09-4.23 (m, 1H), 5.04-5.14 (m, 2H), 5.29-5.39 (m, 1H), 5.71 (d, J=7.63 Hz, 1H), 6.07 (s, 1H), 6.12-6.27 (m, 1H), 7.08-7.26 (m, 5H), 7.27-7.43 (m, 7H), 7.55 (d, J=7.24 Hz, 1H).

(2S)-ethyl 2-((((4R,6R,7S)-4-(4-amino-2-oxopyrimidin-1(2H)-yl)-7-hydroxy-5-oxaspiro[2.4]heptan-6-yl)methoxy)(phenoxy)phosphorylamino)-3-phenylpropanoate

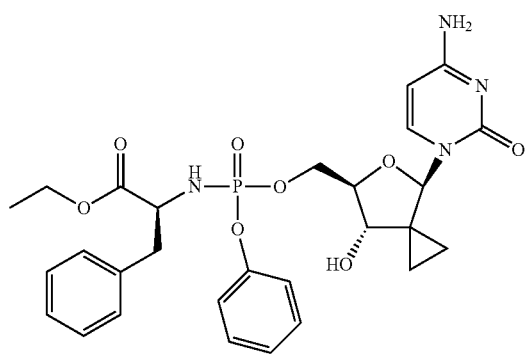

(2c)

LC-MS: Rt: 1.84 min m/z: 585 (M+H)⁺

(2S)-methyl 2-((((4R,6R,7S)-4-(4-amino-2-oxopyrimidin-1(2H)-yl)-7-hydroxy-5-oxaspiro[2.4]heptan-6-yl)methoxy)(phenoxy)phosphorylamino)propanoate (2d)

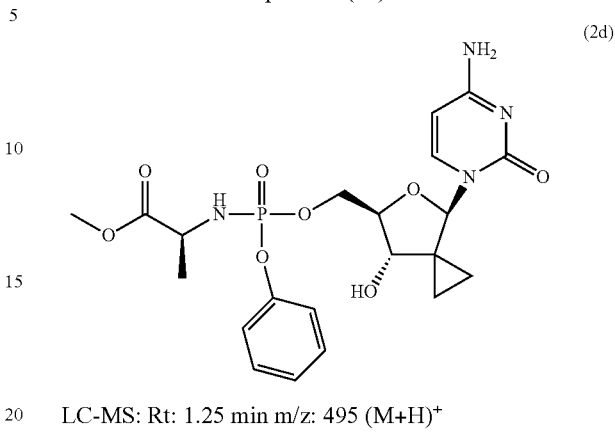

LC-MS: Rt: 1.25 min m/z: 495 (M+H)⁺

Example 3

(4R,6R,7S)-4-(4-amino-2-oxopyrimidin-1(2H)-yl)-6-(isobutyryl-oxymethyl)-5-oxaspiro[2.4]heptan-7-yl isobutyrate (3)

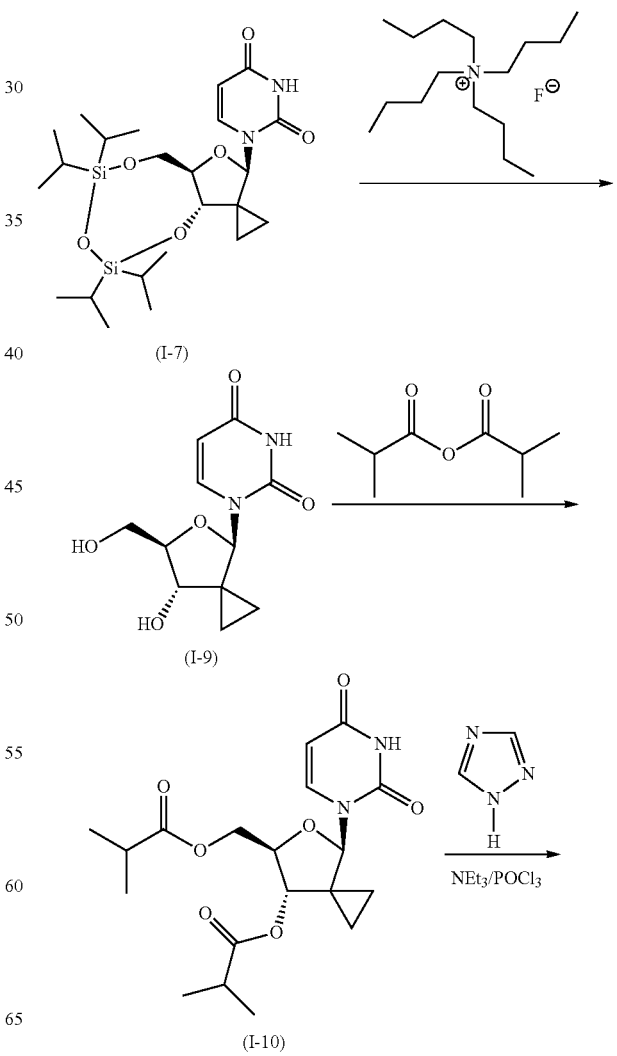

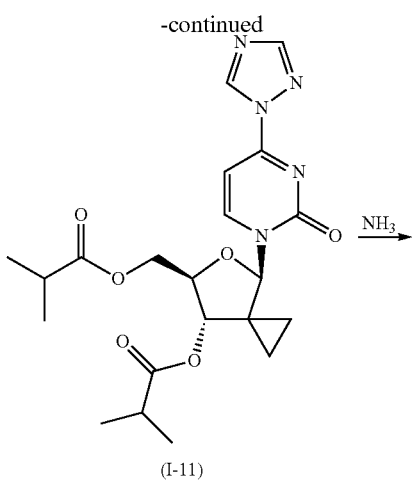

(I-11)

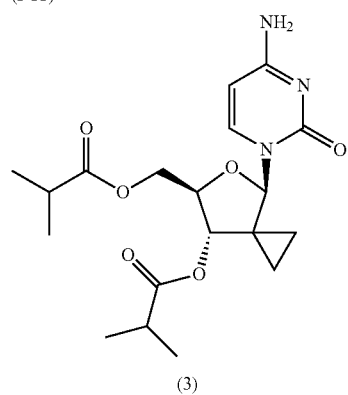

(3)

Intermediate I-7 (11.00 g, 22.14 mmol) was dissolved in THF (280 mL) and TBAF (59.8 mL, 59.8 mmol) was added. The mixture was stirred at room temperature for 1 hour. A mixture of pyridine, methanol and water (80 mL, 3:1:1) was added, followed by a strongly acidic cation exchanger, Dowex 50 Wx4 (128 g), in a mixture of pyridine, methanol and water (320 mL, 3:1:1). The reaction mixture was stirred for 45 minutes and filtrated. The Dowex residue was washed twice with a mixture of pyridine, methanol and water (320 mL, 3:1:1) and the combined filtrates were concentrated under reduced pressure. The mixture was purified by silica gel chromatography by gradient elution 0 to 10% methanol in ethyl acetate, resulting in intermediate I-9 (5.597 g, 84%) as a white foam. LC-MS Rt: 2.05 min, m/z=253 (M−H)⁻.

Intermediate I-9 (5.16 g, 20.30 mmol) was dissolved in dry pyridine (100 mL) and the solution was externally cooled with cold water. Isobutyric anhydride (16.85 mL, 101 mmol) was added and the reaction was allowed to proceed at room temperature overnight. The reaction was again externally cooled with cold water and the excess isobutyric anhydride was quenched by addition of methanol. After stirring for 20 minutes at room temperature and evaporation of the volatiles, ethyl acetate was added and the mixture was washed with saturated aqueous $NaHCO_3$ (2×). The organic phase was dried with $MgSO_4$ and concentrated in vacuo to give I-10 (7.68 g, 96%) as a white solid. LC-MS: Rt: 2.26 min, m/z=393 (M−H)⁻.

$POCl_3$ (4.72 mL, 50.6 mmol) was added to a cooled mixture of I-10 (7.68 g, 19.47 mmol), 1H-1,2,4-triazole (15.20 g, 220 mmol) and triethylamine (30.7 mL, 220 mmol) in dry $CH_2Cl_2$ (50 mL). The mixture was stirred at room temperature for 2.5 hours. The excess $POCl_3$ was quenched by addition of cold water and the organic layer was separated and concentrated in vacuo. The mixture was purified by silica gel chromatography by gradient elution $CH_2Cl_2$/ethyl acetate 90:10 to 85:15, resulting in intermediate I-11 (7.5 g, 86%). LC-MS: Rt: 2.38 min, m/z=446 (M+H)⁺.

Intermediate I-11 (7.49 g, 16.81 mmol) was dissolved in THF (200 mL) and treated with concentrated aqueous $NH_4OH$ (15 mL). After 3.5 hours, the volatiles were removed under reduced pressure. The mixture was purified by silica gel chromategraphy by gradient elution with 0 to 5% methanol in $CH_2Cl_2$. The product was dissolved in ethyl acetate and the mixture was washed with water (2×) and brine (2×). The organic phase was dried with $MgSO_4$ and after filtration, concentrated in vacuo, resulting in compound 3 (5.597 g, 84%) as a white foam. LC-MS: Rt: 1.95 min, m/z=394 (M+H)⁺.

¹H NMR (400 MHz, DMSO-$d_6$) δ ppm 0.36-0.46 (m, 1H) 0.64-0.75 (m, 1H) 0.77-0.92 (m, 2H) 1.06-1.15 (m, 12H) 2.53-2.66 (m, 2H) 4.18-4.36 (m, 3H) 4.98-5.02 (m, 1H) 5.77 (d, J=7.4 Hz, 1H) 6.25 (s, 1H) 7.25 (br. s., 1H) 7.29 (br. s., 1H) 7.55 (d, J=7.4 Hz, 1H)

Example 4

((4R,6R,7S)-4-(4-amino-2-oxopyrimidin-1(2H)-yl)-7-hydroxy-5-oxaspiro[2.4]heptan-6-yl)methyl isobutyrate (4))

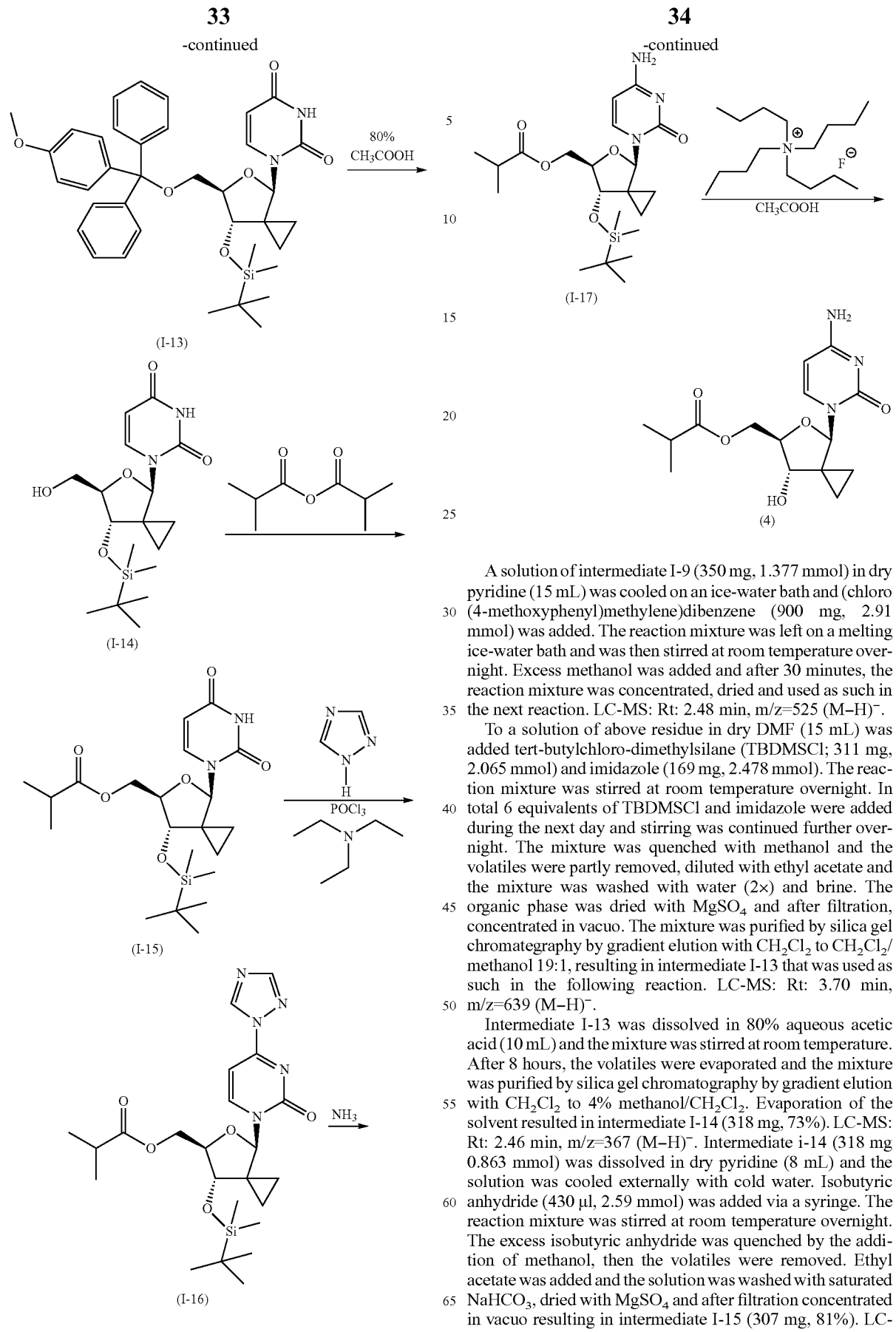

A solution of intermediate I-9 (350 mg, 1.377 mmol) in dry pyridine (15 mL) was cooled on an ice-water bath and (chloro (4-methoxyphenyl)methylene)dibenzene (900 mg, 2.91 mmol) was added. The reaction mixture was left on a melting ice-water bath and was then stirred at room temperature overnight. Excess methanol was added and after 30 minutes, the reaction mixture was concentrated, dried and used as such in the next reaction. LC-MS: Rt: 2.48 min, m/z=525 (M−H)⁻.

To a solution of above residue in dry DMF (15 mL) was added tert-butylchloro-dimethylsilane (TBDMSCl; 311 mg, 2.065 mmol) and imidazole (169 mg, 2.478 mmol). The reaction mixture was stirred at room temperature overnight. In total 6 equivalents of TBDMSCl and imidazole were added during the next day and stirring was continued further overnight. The mixture was quenched with methanol and the volatiles were partly removed, diluted with ethyl acetate and the mixture was washed with water (2×) and brine. The organic phase was dried with $MgSO_4$ and after filtration, concentrated in vacuo. The mixture was purified by silica gel chromategraphy by gradient elution with $CH_2Cl_2$ to $CH_2Cl_2$/methanol 19:1, resulting in intermediate I-13 that was used as such in the following reaction. LC-MS: Rt: 3.70 min, m/z=639 (M−H)⁻.

Intermediate I-13 was dissolved in 80% aqueous acetic acid (10 mL) and the mixture was stirred at room temperature. After 8 hours, the volatiles were evaporated and the mixture was purified by silica gel chromatography by gradient elution with $CH_2Cl_2$ to 4% methanol/$CH_2Cl_2$. Evaporation of the solvent resulted in intermediate I-14 (318 mg, 73%). LC-MS: Rt: 2.46 min, m/z=367 (M−H)⁻. Intermediate i-14 (318 mg 0.863 mmol) was dissolved in dry pyridine (8 mL) and the solution was cooled externally with cold water. Isobutyric anhydride (430 μl, 2.59 mmol) was added via a syringe. The reaction mixture was stirred at room temperature overnight. The excess isobutyric anhydride was quenched by the addition of methanol, then the volatiles were removed. Ethyl acetate was added and the solution was washed with saturated $NaHCO_3$, dried with $MgSO_4$ and after filtration concentrated in vacuo resulting in intermediate I-15 (307 mg, 81%). LC-MS: Rt: 3.0 min, m/z=437 (M−H)⁻.

Intermediate I-15 (307 mg, 0.700 mmol), 1H-1,2,4-triazole (546 mg, 7.91 mmol) and triethylamine (1.1 mL, 7.91 mmol) were dissolved in dry $CH_2Cl_2$ (7 mL) and cooled at 0° C. $POCl_3$ (0.170 mL, 1.820 mmol) was added while the reaction temperature was maintained below 25° C. The mixture was stirred overnight. 3.0 equivalents of 1H-1,2,4-triazole and triethylamine as well as $CH_2Cl_2$ (5 mL) were added and the mixture was stirred for another 3 hours at room temperature. The excess $POCl_3$ was quenched by careful addition of cold water. The lower organic layer was separated and concentrated by evaporation under vacuum. The mixture was purified by silica gel chromatography by gradient elution with $CH_2Cl_2$ to 4% methanol/$CH_2Cl_2$, resulting in intermediate I-16 (200 mg, 58%). LC-MS: Rt: 3.09 min, m/z=490 $(M+H)^+$.

Intermediate I-16 (200 mg, 0.408 mmol) was dissolved in THF (5 mL) and treated with concentrated aqueous $NH_4OH$ (0.5 mL). After 7 hours, the volatiles were removed and the mixture was concentrated under reduced pressure. The mixture was purified by silica gel chromatography by gradient elution with $CH_2Cl_2$ to 5% methanol/$CH_2Cl_2$. After evaporation of the solvent, intermediate I-17 (179 mg, 100%) was obtained. LC-MS: Rt: 2.74 min, m/z=438 $(M+H)^+$.

To a solution of intermediate I-17 (179 mg, 0.409 mmol) and acetic acid (147 mg, 2.454 mmol) in THF (10 mL), was added TBAF (1227 µL, 1.227 mmol, 1M in THF). The mixture was stirred at room temperature. Stirring was continued for 2 hours and the solvent was then removed. The mixture was purified by silica gel chromatography by gradient elution with methanol/$CH_2Cl_2$ 4% to 8%. The product (100 mg) was mixed with $CaCO_3$ (60 mg) and Dowex 50 Wx4 (200 mg) in THF (10 mL) and stirred at room temperature for 2 hours. The mixture was filtrated and after evaporation of the volatiles, repurified by silica gel chromatography (gradient elution: 0 to 15% methanol in chloroform), resulting in compound 4 as a white solid (59 mg, 44%) LC-MS: Rt: 1.08 min, m/z=324 $(M+H)^+$.

$^1$H NMR (400 MHz, DMSO-$d_6$) δ ppm 0.36-0.45 (m, 1H) 0.46-0.57 (m, 2H) 0.96-1.05 (m, 1H) 1.10 (d (app.)), J=6.5 Hz, 6H) 2.58 (h(app.)), J=6.5 Hz, 1H) 3.86-3.91 (m, 1H) 3.97-4.01 (m, 1H) 4.21 (dd, J=12.0, 5.9 Hz, 1H) 4.33 (dd, J=12.0, 2.3 Hz, 1H) 5.34 (d, J=5.7 Hz, 1H) 5.74 (d, J=7.4 Hz, 1H), 6.01 (s, 1H) 7.06-7.28 (m, 2H) 7.57 (d, J=7.4 Hz, 1H).

Example 5

(4R,6R,7S)-4-(4-amino-2-oxopyrimidin-1(2H)-yl)-6-(hydroxymethyl)-5-oxaspiro[2.4]heptan-7-yl isobutyrate (5)

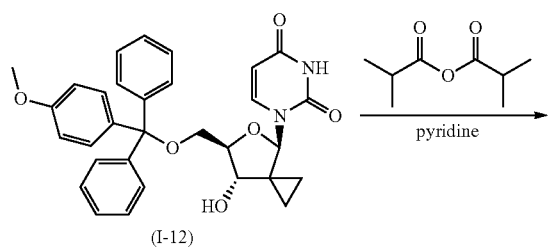

(I-12)

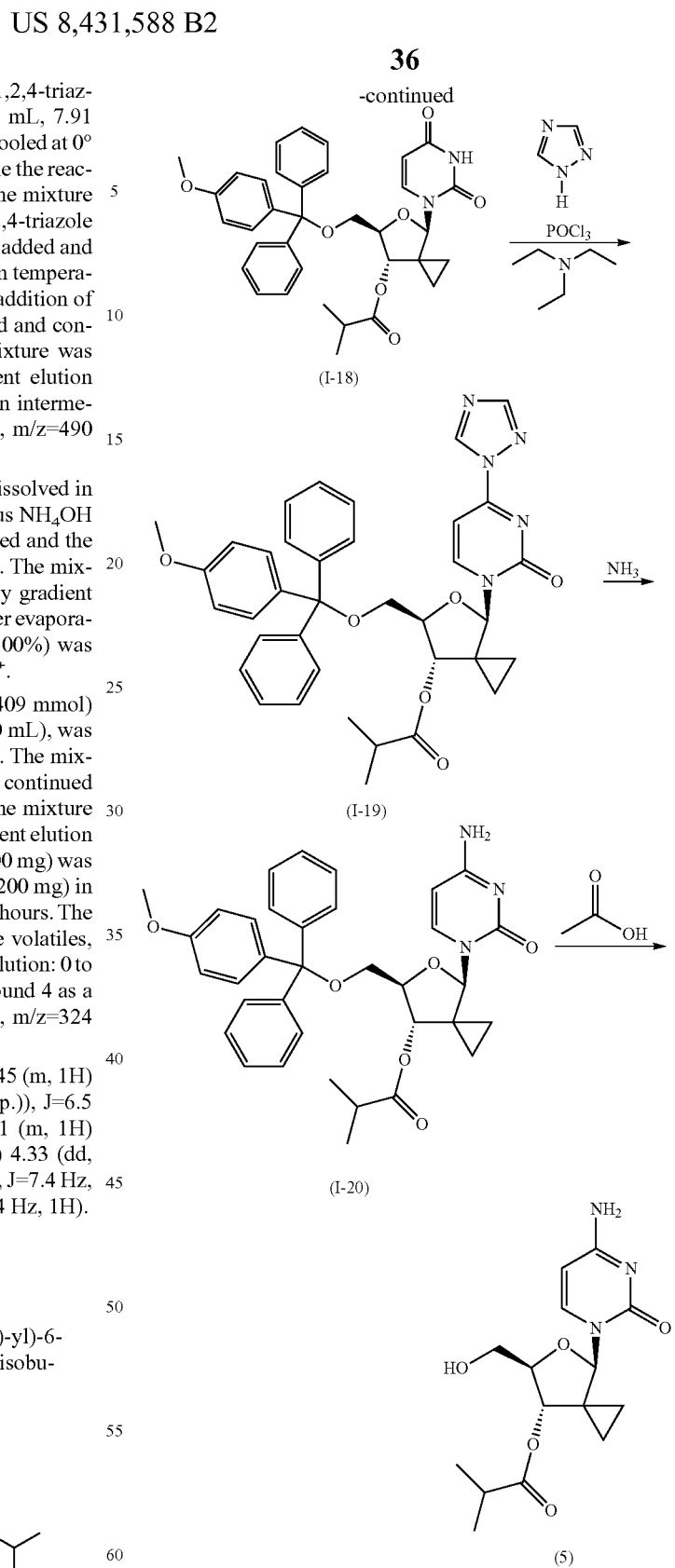

Intermediate I-12 (250 mg, 0.475 mmol) was dissolved in dry pyridine (10 mL) and the solution externally cooled with cold water. To the solution was added via syringe isobutyric anhydride (236 µl, 1.424 mmol), and the reaction was stirred at room temperature for 2 hours. More isobutyric anhydride (236 µl, 1.424 mmol) was added and the mixture was further stirred for 2 hours. More isobutyric anhydride (236 μl, 1.424 mmol) was added and the mixture was stirred overnight. Subsequently, the excess isobutyric anhydride was quenched by addition of methanol. The solution was stirred for 20 minutes at room temperature and then concentrated to dryness. The residue was taken into ethyl acetate (30 mL) and the solution washed with saturated aqueous NaHCO$_3$ (2×20 mL). The organic phase was dried over Na$_2$SO$_4$, the solid was filtered off and the solvent removed by evaporation. Resulting in I-18 as a colorless oil, used as such in the next reaction. LC-MS: Rt: 3.07 min.

POCl$_3$ (102 μl, 1.089 mmol) was added to a cooled mixture of intermediate I-18 (250 mg, 0.419 mmol), 1H-1,2,4-triazole (327 mg, 4.73 mmol), triethylamine (661 μl, 4.73 mmol), and CH$_2$Cl$_2$ (6.0 mL) while the reaction temperature was maintained below 25° C. (resulting in a white precipitation). The reaction mixture was stirred at room temperature for 4 hours. When the reaction was completed, the excess POCl$_3$ was quenched by careful addition of cold H$_2$O. The organic layer was separated and concentrated by evaporation under vacuum. The mixture was purified by silica gel chromatography by gradient elution CH$_2$Cl$_2$/ethyl acetate 90:10 to 85:15 resulting in intermediate I-19 as an oil (200 mg, 74%): Rt: 3.15 min.

Intermediate I-19 (200 mg, 0.309 mmol) was dissolved in THF (5 mL) and treated with concentrated aqueous NH$_4$OH (0.6 mL). After 4 hours more concentrated aqueous NH$_4$OH (0.3 mL) was added and the mixture was stirred overnight. The solvent was removed in vacuo, the oil was taken up in ethyl acetate and washed with water and brine. After drying with Na$_2$SO$_4$, filtration and evaporation of the volatiles, the residue (I-20) was used as such in the next reaction. LC-MS: Rt: 2.86 min, m/z=594 (M–H)$^-$. Intermediate I-20 (180 mg, 0.302 mmol) was dissolved in 80% aqueous acetic acid (5 mL) and the reaction mixture was stirred at room temperature. After 9 hours, the volatiles were removed and the mixture was purified by silica gel chromatography by gradient elution with 5% to 15% methanol in CH$_2$Cl$_2$. The obtained residue was triturated with iPr$_2$O and dried in vacuo. Resulting in compound 5 (60.8 mg, 62%). LC-MS: Rt: 1.25 min, m/z=324 (M+H)$^+$.

$^1$H NMR (400 MHz, DMSO-d$_6$) δ ppm 0.33-0.41 (m, 1H) 0.62-0.71 (m, 1H) 0.74-0.82 (m, 2H) 1.08-1.14 (m, 6H) 2.55-2.64 (1H, m) 3.62-3.68 (m, 2H) 3.99-4.04 (m, 1H) 4.98-5.03 (m, 1H) 5.12 (t, J=5.2 Hz, 1H) 5.76 (d, J=7.4 Hz, 1H) 6.27 (s, 1H) 7.14-7.33 (m, 2H) 7.80 (d, J=7.4 Hz, 1H)

Example 6

The isobutyryl ester of (2S)-benzyl 2-(((((4R,6R,7S)-4-(4-amino-2-oxo-pyrimidin-1(2H)-yl)-7-hydroxy-5-oxaspiro[2.4]heptan-6-yl)methoxy) (phenoxy) phosphoryl-amino)propanoate (6)

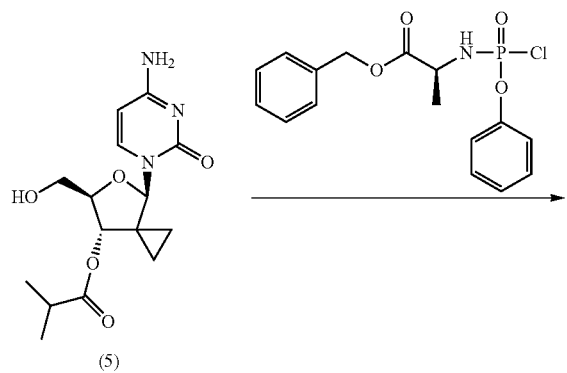

(5)

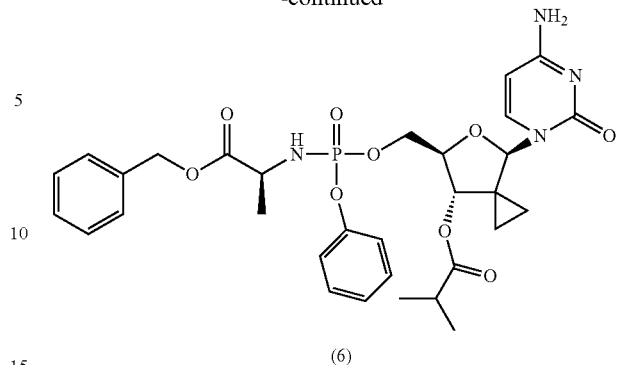

(6)

Compound 5 is dissolved in dry THF/pyridine together with (2S)-benzyl 2-(chloro-(phenoxy)phosphorylamino)propanoate (2.0 eq). The mixture is cooled to –78° C. N-methylimidazole (NMI) (8 eq) is added and the mixture is stirred for 15 minutes at –78° C. and then stirred at RT overnight. The mixture is evaporated to dryness. 10 mL CH$_2$Cl$_2$ is added and the residue is washed with 10 mL 0.5N HCl. The organic layer is separated and washed with 10 mL water, dried on Na$_2$SO$_4$, filtered and evaporated. The compound is purified by silica gel chromatography using a gradient of CH$_2$Cl$_2$/MeOH as the eluent.

Following the same procedures but starting from (2S)-ethyl 2-(chloro-(phenoxy)phosphorylamino)propanoate there is also prepared the isobutyryl ester of (2S)-ethyl 2-(((((4R,6R,7S)-4-(4-amino-2-oxo-pyrimidin-1(2H)-yl)-7-hydroxy-5-oxaspiro[2.4]heptan-6-yl)methoxy) (phenoxy) phosphoryl-amino)propanoate (7):

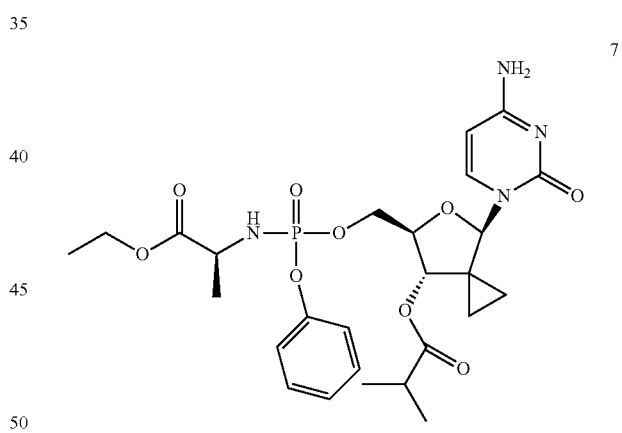

7

Biological Examples

Replicon Assay

The compounds of formula I were examined for activity in the inhibition of HCV RNA replication in a cellular assay aimed at identifying compounds that inhibit a HCV functional cellular replicating cell line, also known as HCV replicons. The cellular assay was based on a bicistronic expression construct, as described by Lohmann et al. (1999), Science vol. 285 pp. 110-113 with modifications described by Krieger et al. (2001), Journal of Virology 75: 4614-4624, in a multi-target screening strategy.

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct is bordered by 5' and 3' NTRs (non-translated regions) from HCV type 1b. Continued culture of the replicon cells in the presence of G418 (neo$^R$) is dependent on the replication of the HCV RNA. The stably transfected replicon cells that express HCV RNA, which replicates autonomously and to high levels, encoding inter alia luciferase, were used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. EC50 values were then calculated, which value represents the amount of the compound required to decrease the level of detected luciferase activity by 50%, or more specifically, the ability of the genetically linked HCV replicon RNA to replicate.

Cellular Toxicity

Cellular toxicity was determined in the Huh7-CMV-Luc replicon assay. Replicon cells (2500 cells/well), stably transformed with a luciferase reporter gene under control of the cytomegalovirus (CMV) constitutive promotor, were cultured in the presence or absence of test compound concentrations. After three days of incubation at 37° C. in a humidified 5% $CO_2$ atmosphere, cell proliferation was quantified by measuring the Luc activity, and expressed as $CC_{50}$ values (cytotoxicity, 50% inhibitory concentration of cell growth). Tests were performed in 384-well plates.

HIV Assay

Compounds of the invention were tested for their potency against wild type human immunodeficiency virus (HIV). Antiviral activity was evaluated using a cellular assay performed according to the following procedure. The human T-cell line MT4 was engineered with Green Fluorescent Protein (GFP) and a HIV-specific promoter, HIV-1 long terminal repeat (LTR). This cell line, designated MT4 LTR-EGFP, can be used for the in vitro evaluation of anti-HIV activity of investigational compounds. In HIV-1 infected cells, the Tat protein is produced, which upregulates the LTR promotor and eventually leads to stimulation of the GFP reporter production, allowing to measure ongoing HIV-infection fluorometrically. Effective concentration values such as 50% effective concentration (EC50) can be determined and are usually expressed in µM. An EC50 value is defined as the concentration of test compound that reduces the fluorescence of HIV-infected cells by 50%. Monitoring of HIV-1 infection was done using a scanning microscope. Image analysis allows very sensitive detection of viral infection. Measurements were done before cell necrosis, which usually takes place about five days after infection, in particular measurements were performed three days after infection. The column IIIB in the table list the $EC_{50}$ values against the wild type strain IIIB.

The results in the following table illustrate that compounds of the present invention show activity against HCV, while lacking activity against HIV. They show favorable results in terms of toxicity and have an acceptable selectivity index (ratio between $EC_{50}$ and $CC_{50}$).

TABLE

Test Results

| Compound number | $EC_{50}$ (replicon) µM | $CC_{50}$ (Huh7) µM | $EC_{50}$ (IIIB) µM |
|---|---|---|---|
| 1 | 8.4 | >98 | >98 |
| 2a | 15.3 | >98 | >98 |
| 2b | 26.3 | >98 | >98 |
| 2c | 98 | >98 | >98 |
| 2d | 63.1 | >98 | >98 |
| 3 | 27.2 | >98 | >98 |
| 4 | 9.2 | >98 | >98 |
| 5 | 42.5 | >98 | >98 |

The invention claimed is:

1. A compound of formula I:

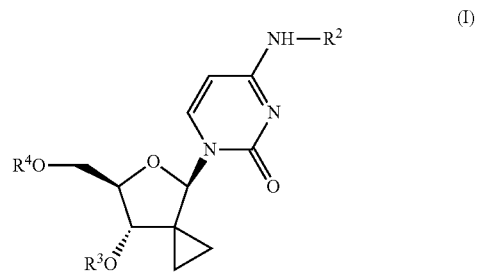

including any possible stereoisomers thereof, wherein:
$R^2$ is hydrogen or $C_1$-$C_4$alkyl;
$R^3$ and $R^4$ are independently selected from the group consisting of hydrogen, —C(=O)$R^5$, and —C(=O)CHR$^6$—NH$_2$; or
$R^3$ is hydrogen and $R^4$ is a monophosphate-, diphosphate-, or triphosphate ester; or $R^3$ is hydrogen, —C(=O)CHR$^5$, or —C(=O)CHR$^6$—NH$_2$ and $R^4$ is a group of formula

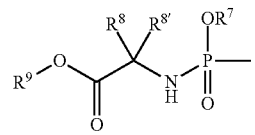

each $R^5$ is independently selected from the group consisting of hydrogen, $C_1$-$C_6$alkyl, and $C_3$-$C_7$cycloalkyl;
$R^6$ is hydrogen or $C_1$-$C_6$alkyl;
$R^7$ is phenyl, optionally substituted with 1, 2 or 3 substituents each independently selected from halo, $C_1$-$C_6$alkyl, $C_3$-$C_6$alkenyl, $C_1$-$C_6$alkoxy, hydroxy, and amino, or $R^7$ is naphthyl; or $R^7$ is indolyl;
$R^8$ is hydrogen, $C_1$-$C_6$alkyl, benzyl;
$R^{8'}$ is hydrogen, $C_1$-$C_6$alkyl, benzyl; or
$R^8$ and $R^{8'}$ together with the carbon atom to which they are attached form $C_3$-$C_7$cycloalkyl;
$R^9$ is $C_1$-$C_6$alkyl, benzyl, or phenyl, wherein said phenyl may be optionally substituted with 1, 2 or 3 substituents each independently selected from hydroxy, $C_1$-$C_6$alkoxy, amino, mono- and di$C_1$-$C_6$alkylamino;
provided that $R^2$, $R^3$ and $R^4$ are not all hydrogen;
or a pharmaceutically acceptable salt thereof.

2. The compound according to claim 1, wherein $R^2$ is hydrogen.

3. The compound according to claim 1, wherein $R^3$ and $R^4$ are hydrogen.

4. The compound according to claim 1 wherein $R^3$ is hydrogen and $R^4$ is a group of formula

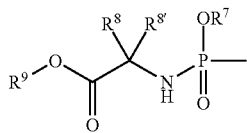

5. The compound according to claim 1 wherein $R^7$ is phenyl, optionally substituted with halo, or $C_1$-$C_6$alkyl, or $R^7$ is naphthyl.

6. The compound according to claim 1 wherein $R^8$ is hydrogen, and $R^{8'}$ is hydrogen or $C_1$-$C_6$alkyl.

7. The compound according to claim 1 wherein one of $R^3$ and $R^4$ is —C(═O)$R^5$ and the other of $R^3$ and $R^4$ is hydrogen; or wherein both $R^3$ and $R^4$ are —C(═O)$R^5$; and wherein $R^5$ is $C_1$-$C_6$alkyl.

8. The compound of claim 7 wherein $R^5$ is isopropyl.

9. The compound according to claim 1 wherein $R^9$ is $C_1$-$C_6$alkyl or benzyl.

10. The compound of claim 1, wherein the compound has the formula:

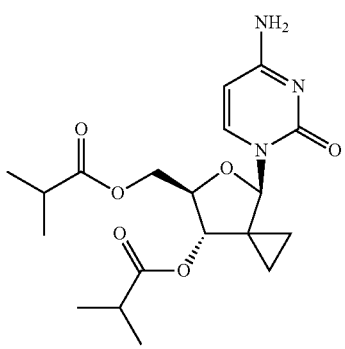 [SMILES: CC(C)C(=O)OC[C@H]1O[C@@H](n2ccc(N)nc2=O)C2(CC2)[C@@H]1OC(=O)C(C)C]

11. The compound of claim 10, wherein the compound is in free form.

12. A pharmaceutical composition comprising an anti-virally effective amount of a compound of formula I as defined in claim 1 and a pharmaceutically acceptable carrier.

13. The method of inhibiting HCV in a subject in need of such inhibition comprising administering to said subject an effective amount of a compound of formula I,

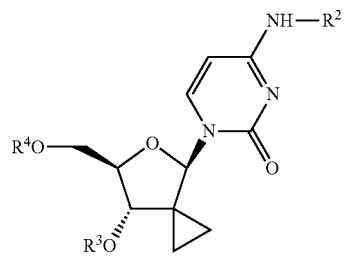

including any possible stereoisomers thereof, wherein:
$R^2$ is hydrogen or $C_1$-$C_4$alkyl;
$R^3$ and $R^4$ are independently selected from the group consisting of hydrogen, —C(═O)$R^5$, and —C(═O)CHR$^6$—NH$_2$; or
$R^3$ is hydrogen and $R^4$ is a monophosphate-, diphosphate-, or triphosphate ester; or $R^3$ is hydrogen, —C(═O)CHR$^5$, or —C(═O)CHR$^6$—NH$_2$ and $R^4$ is a group of formula

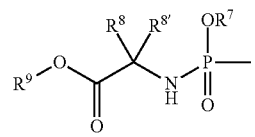

each $R^5$ is independently selected from the group consisting of hydrogen, $C_1$-$C_6$alkyl, and $C_3$-$C_7$cycloalkyl;
$R^6$ is hydrogen or $C_1$-$C_6$alkyl;
$R^7$ is phenyl, optionally substituted with 1, 2 or 3 substituents each independently selected from halo, $C_1$-$C_6$alkyl, $C_3$-$C_6$alkenyl, $C_1$-$C_6$alkoxy, hydroxy, and amino, or $R^7$ is naphthyl; or $R^7$ is indolyl;
$R^8$ is hydrogen, $C_1$-$C_6$alkyl, benzyl;
$R^{8'}$ is hydrogen, $C_1$-$C_6$alkyl, benzyl; or
$R^8$ and $R^{8'}$ to ether with the carbon atom to which the are attached form $C_3$-$C_7$cycloalkyl;
$R^9$ is $C_1$-$C_6$alkyl, benzyl, or phenyl, wherein said phenyl may be optionally substituted with 1, 2 or 3 substituents each independently selected from hydroxy, $C_1$-$C_6$alkoxy, amino, mono- and di$C_1$-$C_6$alkylamino;
provided that $R^2$, $R^3$ and $R^4$ are not all hydrogen;
or a pharmaceutically acceptable salt thereof.

14. The method of claim 13 wherein the compound of formula 1 has $R^2$, $R^3$ and $R^4$ all hydrogen.

15. The method of claim 14 in which the compound is in free form.

16. A pharmaceutical composition as defined in claim 12 in combination with another HCV inhibitor.

* * * * *